United States Patent [19]

Nishikawa et al.

[11] Patent Number: 5,763,408
[45] Date of Patent: Jun. 9, 1998

[54] AMINO ACID DERIVATIVES AND APPLICATION THEREOF

[75] Inventors: Naoyuki Nishikawa; Atsushi Orikasa, both of Minami-ashigara; Hiroyuki Komazawa, Asaka; Masayoshi Kojima, Minami-ashigara; Ikuo Saiki, Toyama; Ichiro Azuma, Sapporo, all of Japan

[73] Assignee: Fuji Photo Film Co., Ltd., Kanagawa, Japan

[21] Appl. No.: 392,258

[22] Filed: Feb. 22, 1995

Related U.S. Application Data

[63] Continuation-in-part of Ser. No. 343,520, filed as PCT/JP93/00734 Jun. 1, 1993, abandoned.

[30] Foreign Application Priority Data

Jun. 3, 1992 [JP] Japan ................................. 4-142607
May 21, 1993 [JP] Japan ................................. 5-119848

[51] Int. Cl.$^6$ ................................................. A61K 38/03
[52] U.S. Cl. ........................................................... 514/18
[58] Field of Search ............................ 562/560, 439; 560/168; 544/196; 530/330, 331, 323, 345; 514/18

[56] References Cited

FOREIGN PATENT DOCUMENTS

92/13552  8/1992  WIPO ................................. 530/12
WO 93/24448  9/1993  WIPO.

OTHER PUBLICATIONS

Pierschbachel et al., "Influence Stereochemistry R–G–D–$X_{xa}$ on Binding in Cell Adhesion", J. Biol. Chem., v. 262, N. 36, pp. 17294–17298. (1987).

Goodman et al., "Concept of Linear Modified Retro–Peptide stimulants", All. Chem. Res., v. 12, N. 1, pp. 1–7. (1979).

Ali et al., "Anti Aggregatory Peptides" (20 Aug. 1992) Chem Abs 118:7397.

Primary Examiner—Cecilia J. Tsang
Assistant Examiner—Patrick R. Delaney
Attorney, Agent, or Firm—Sughrue, Mion, Zinn, Macpeak & Seas, PLLC

[57] ABSTRACT

There are disclosed amino acid derivatives represented by the following general formula (I):

General formula (I)

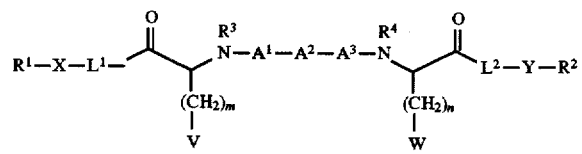

wherein $L^1$ and $L^2$ represent an amino acid residue etc., $A^1$ and $A^3$ represent C=O, $A^2$ represents an alkylene group etc., m and n represent an integer of 1 to 5, V represents —NHC(=NH)NH$_2$ etc., W represents —COOH etc., $R^1$ and $R^2$ represent hydrogen atom, alkyl group etc., $R^3$ and $R^4$ represent hydrogen etc. and X and Y represent —NH— or —O— and pharmaceutically acceptable salts thereof and agents for inhibiting tumor matastasis containing the compounds, and the amino acid derivatives exhibit high activity for inhibiting tumor metastasis and weak platelet aggregation inhibition activity and weak anticoagulation activity.

21 Claims, 1 Drawing Sheet

AMINO ACID DERIVATIVES AND APPLICATION THEREOF

CROSS REFERENCE TO RELATED APPLICATIONS

This is a Continuation-in-Part of application Ser. No. 08/343,520 now abandoned filed Jan. 24, 1995, which is a 371 application of PCT Application No. PCT/JP93/00734, filed Jun. 1, 1993.

FIELD OF THE INVENTION

The present invention relates to amino acid derivatives having high activity for inhibiting tumor metastasis, weak activity for inhibiting platelet aggregation and weak anticoagulation activity.

BACKGROUND ART

Fibronectin and vitronectin are proteins referred as extracellular matrix molecules and involved in the cell-extracellular substrate adhesion. Recently, it was found that these interactions are mediated by a series of receptors present on cell surfaces and that Arg-Gly-Asp sequences in the cell adhesion domains of fibronectin act as recognition sites (Nature, 309, 1984, p30) and it was reported that one of the cell receptors is VLA-5 receptor which belongs to the integrin family. It has been also known that the Arg-Gly-Asp sequences are present in other adhesive proteins such as vitronectin.

Further, the extracellular matrix molecules are considered to adhere to the receptors of cells to be adhered and transmit their information to the adhered cells. In addition, they are also considered to have abilities for bonding to biological macromolecules such as heparin, collagen and fibrin and to be involved in adhesion between cells and interstitial connective tissue, cell differentiation and cell proliferation.

Further, the extracellular matrix molecules are expected to be involved in adhesion and release of tumor cells observed in tumor metastasis. Therefore, there have been reported attempts to inhibit tumor metastasis by using peptides containing the recognition sequence, Arg-Gly-Asp. Yamada et al. demonstrated that the adhesion signal of fibronectin, a pentapeptide (Gly-Arg-Gly-Asp-Ser), inhibits experimental metastasis of B16-F10 melanoma cells to lungs (Science, Vol. 233 (1986) p467). Further, there have been disclosed methods for more efficient inhibition of tumor metastasis by using oligopeptides containing the sequence or polypeptides containing the sequences as repeating units (Int. J. Biol. Macromol., Vol. 11 (1989), p23; Int. J. Biol. Macromol., Vol. 11 (1989), p226; Jpn. J. Cancer Res., Vol. 60 (1989), p722; and Japanese Patent Un-examined Publication (KOKAI) No. Hei 2-174789).

It has been also known that peptides containing the Arg-Gly-Asp sequence inhibit platelet aggregation. It is considered that platelet aggregation is caused by bondings of Von Willebrand factors, plasma proteins and fibrinogen mainly to the platelet receptors present on platelets referred to as GPIIb/IIIa, which bondings form a crosslinking structure. Fibronectin, vitronectin and thrombospondine are examples of the proteins which bond to GPIIb/IIIa. Nievelstein et al. reported that peptides containing Arg-Gly-Asp-Ser sequences inhibit thrombin-induced aggregation and adhesion of platelets to fibronectin and that there is a possibility that they show such activities through GPIIb/IIIa complexes (Thrombosis and Hemostasis, Vol. 58 (1987), p2133).

Further, interactions of the Arg-Gly-Asp sequence with various receptors such as VLA-5, VLA-3, VNR and GPIIb/IIIa have also been known and their various physiological activities have been reported. However, multiplicity of these activities has been considered a drawback from the viewpoint of selectivity. That is, when peptide derivatives having the Arg-Gly-Asp sequence are used for inhibiting metastasis of tumor cells, their high platelet aggregation inhibiting activity and anticoagulation activity may cause problems.

In addition, peptide drugs have a drawback that they are easily degraded by blood protease in living bodies and hence their pharmaceutical activities are lost. It is known that the Arg-Gly bond of the Arg-Gly-Asp sequence, which is the bonding site for fibronectin, is particularly easily cleaved.

Therefore, tripeptide Arg-Gly-Asp has a drawback of extremely low stability in blood stream.

To solve this problem, there have been attempts to prolong lifetime of physiologically active peptides by using such peptides containing reversed peptide bonds.

There can be mentioned the following examples of such attempts with respect to the peptides containing Arg-Gly-Asp sequences.

The U.S. Pat. No. 5,100,875 discloses Arg-Gly-Asp derivatives containing reversed peptide bonds between two of their amino acid residues. Further, WO092/13552 discloses aromatic esters and amides of Arg-Gly-Asp containing reversed amide bonds between the arginine residues and the glycine residues.

Those compounds have been developed as agents for inhibiting platelet aggregation or antithrombosis agents and hence they have extremely high activity for inhibiting platelet aggregation and anticoagulation activity. However, it has not been known that those compounds have activity for inhibiting tumor metastasis and, even though they have activity for inhibiting tumor metastasis, it is obvious that their high activity for inhibiting platelet aggregation and anticoagulation activity would cause problems.

Further, the activity for inhibiting tumor metastasis is an activity which cannot be necessarily expected from the activity for inhibiting platelet aggregation confirmed in vitro.

WO/00995 discloses agents for controlling cell adhesion comprising cyclic compounds containing the Arg-Gly-Asp sequences wherein the peptide bonds between the arginine residues and the glycine residues are reversed. There is disclosed that those agents for controlling cell adhesion are effective to inhibit platelet aggregation and to treat various diseases involving cell adhesion such as reobstruction by thrombosis. Therefore, when they are used as agents for inhibiting metastasis of tumor, they have a problem from the viewpoint of selectivity.

The object of the present invention is to provide amino acid derivatives which show high activity for inhibiting tumor metastasis and weak activity for inhibiting platelet aggregation and weak anticoagulation activity and are difficult to be degraded under biochemical conditions, and agents for inhibiting tumor metastasis containing them as active ingredients.

SUMMARY OF THE INVENTION

To achieve the above object, the inventors of the present invention had conducted researches of novel amino acid derivatives referring to the cell adhesion core of fibronectin, the Arg-Gly-Asp sequence, as a guidance. As a result, the inventors of the present invention had found amino acid derivatives which exhibit higher tumor metastasis inhibition activity and lower platelet aggregation inhibition activity and anticoagulation activity, which may cause side effects, as compared with the conventional Arg-Gly-Asp-Ser (RGDS). Further, as a result of in vitro experiments, it has been revealed that the compounds of the present invention are stable in blood without being degraded by enzymes and the like, and thus the present invention have been completed.

The above object has been achieved by 1) amino acid derivatives represented by the following general formula (I) or pharmaceutically acceptable salts thereof and compounds composed of macromolecular carriers or organic molecules to which a plural number of the amino acid derivatives of the formula (I) are bonded by covalent bonds or pharmaceutically acceptable salts thereof, and 2) agents for inhibiting tumor metastasis comprising an amino acid derivative represented by the formula (I) or a pharmaceutically acceptable salt thereof as an active ingredient.

General formula (I)

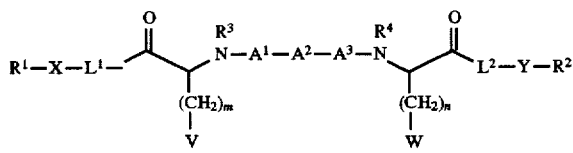

In the formula, $L^1$ and $L^2$ represent a residue which may be present or absent and, when they are present, they independently represent a natural or synthetic amino acid residue or a peptide residue.

$A^1$ and $A^3$ represent C=O, and $A^2$ represents a linear α branched alkylene group having 1 to 5 carbon atoms or a cyclic alkylene group having 4 to 8 carbon atoms or phenylene group, which may have one or more substituents and unsaturated groups. $A^1$, $A^2$ and $A^3$ may be present or absent, provided that at least one of $A^1$, $A^2$ and $A^3$ must be present.

m and n represent an integer of 1 to 5 and they may be the same or different from each other.

V represents —NHC(=NH)NH$_2$, —C(=NH)NH$_2$, —NH$_2$, —NHC(=NH)NHC(=NH)NH$_2$, or a 5- or 6-membered ring containing 1 to 5 nitrogen atoms.

W represents —COOH, —CONH$_2$, —OSO$_3$H or —OPO$_3$H$_2$.

$R^1$ and $R^2$ independently represent hydrogen atom, linear or branched alkyl, aryl, arylalkyl group or a heterocyclic residue, which may have one or more substituents and unsaturated groups.

$R^3$ and $R^4$ independently represent hydrogen atom or methyl group.

X and Y independently represent —NH— or —O—.

Steric configurations of asymmetric carbon atoms present in the compounds may be any of R, S and RS.

Those compounds of the formula (I) wherein both of $L^1$ and $L^2$ are absent and both of $A^1$ and $A^3$ are C=O, $A^2$ is —CH$_2$—, X is —NH—, and $R^2$ is phenyl group, naphthyl group or heterocyclic residue, which may have 1 to 3 substituents, are excluded from the compounds of the present invention.

BEST MODE FOR CARRYING OUT THE INVENTION

Figure 1:
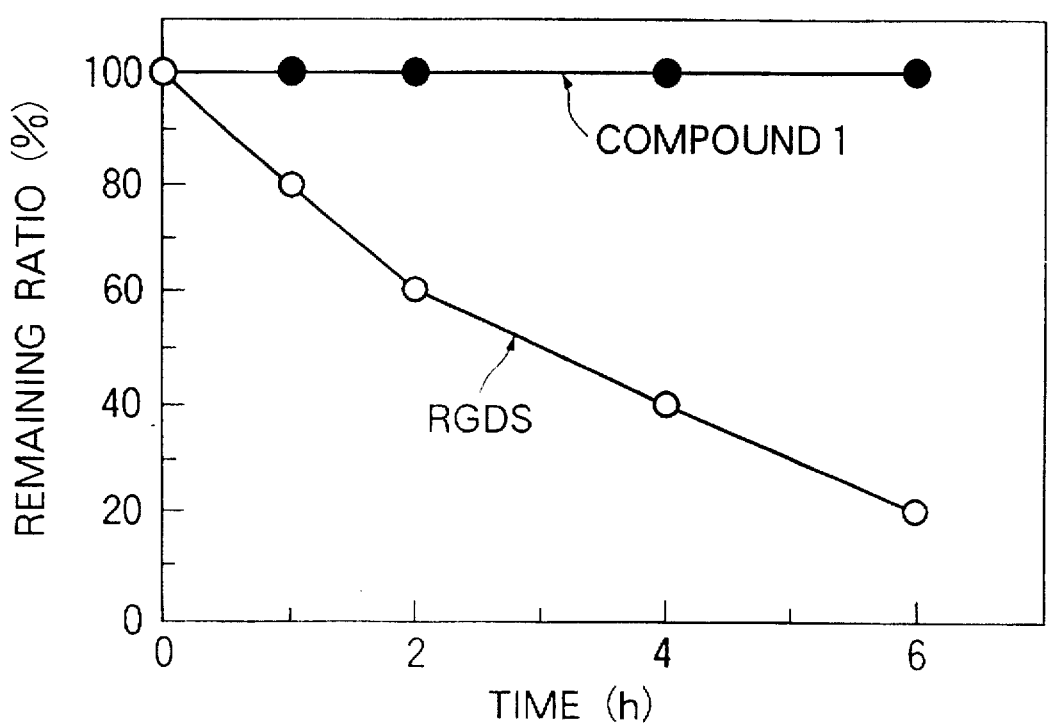
FIG. 1 is a graph which shows results of stability evaluation of Compound 1 and a comparative compound, RGDS peptide, under the biochemical degrading condition of Example 44.

In the formula, $L^1$ and $L^2$ represent a residue which may be present or absent and, when they are present, they independently represent an amino acid residue or a peptide residue. The amino acid residue may be of an amino acid not naturally occurring such as β-alanine and norleucine or amino-acid derivatives.

When $L^1$ is an amino acid residue, it is preferably glycine, lysine, arginine, aspartic acid or glutamic acid residue. Glycine and arginine residues are particularly preferred. Further, when $L^1$ is a peptide residue, it preferably contains one or more of glycine, lysine, arginine, aspartic acid and glutamic acid residues as constituent residues.

When $L^2$ is an amino acid residue, it is preferably serine, threonine, aspartic acid or glutamic acid residue. Serine residue is particularly preferred. When $L^2$ is a peptide residue, it preferably contains one or more of serine, threonine, aspartic acid and glutamic acid residues as constituent residues.

$A^1$ and $A^3$ represent C=O.

$A^2$ represents a linear or branched alkylene group having 1 to 5 carbon atoms, a cyclic alkylene group having 4 to 8 carbon atoms or phenylene group, which may have one or more of substituents and unsaturated groups. When $A^2$ is an alkylene group, it preferably contains 1 to 3 carbon atoms.

Preferred examples of $A^2$ include —CH$_2$—, —(CH$_2$)$_2$—, —(CH$_2$)$_3$—, —CH=CH—, —C(CH$_3$)$_2$— and —C$_6$H$_4$—. Particularly preferred are —CH$_2$—, —(CH$_2$)$_2$—, —CH=CH— and —C$_6$H$_4$—.

Each of $A^1$, $A^2$ and $A^3$ may be absent, but at least one of $A^1$, $A^2$ and $A^3$ must be present.

Preferred $A^1$—$A^2$—$A^3$ are —CO—CH$_2$—CO—, —CO—(CH$_2$)$_2$—CO—, —CO—(CH$_2$)$_3$—CO—, —CO—CH=CH—CO—, —CO—C(CH$_3$)$_2$—CO—, —CO—C$_6$H$_4$—CO—, —CO—, —CO—CO—, —CO—CH$_2$—, —CH$_2$—CO—, —CH$_2$—CH$_2$—CO— and —CO—CH$_2$—CH$_2$—, and particularly preferred $A^1$—$A^2$—$A^3$ are —CO—CH$_2$—CO—, —CO—(CH$_2$)$_2$—CO—, —CO—CH=CH—CO— and —CO—C$_6$H$_4$—CO—.

m and n represents an integer of 1 to 5. m and n may be the same or different. Preferably, m is 3 or 4 and n is 1 to 3, and, particularly, m is 3 and n is 1.

V represents guanidino group (—NHC(=NH)NH$_2$), amidino group (—C(=NH)NH$_2$), amino group (—NH$_2$), biguanide group (—NHC)(=NH)NHC(=NH)NH$_2$ or a 5- or 6-membered ring containing 1 to 5 nitrogen atoms. V preferably represents guanidino group or amino group, and particularly preferably represents guanidino group.

W represents —COOH, —CONH$_2$, —OSO$_3$H or —OPO$_3$H$_2$. Particularly preferred W is carboxyl group (—COOH).

$R^1$ and $R^2$ represent hydrogen atom, linear or branched alkyl, aryl, arylalkyl (aralkyl) group or a heterocyclic residue, which may have one or more substituents and unsaturated groups. $R^1$ and $R^2$ may be the same or different. When $R^1$ and $R^2$ are not hydrogen atom, they preferably have 1 to 20 carbon atoms, particularly up to 8 carbon atoms.

$R^3$ and $R^4$ represent hydrogen atom or methyl group. $R^3$ and $R^4$ are the same or different from each other. $R^3$ and $R^4$ are preferably hydrogen atoms.

X and Y represents —NH— or —O—, and X and Y may be the same or different from each other. It is preferred that both or one of $R^1$—X— and $R^2$—Y— are hydroxyl groups.

When $R^1$—X— or $R^2$—Y— is not a hydroxyl group, it is preferred that $L^1$ or $L^2$ is present and represents a glutamic acid residue.

Steric configurations of asymmetric carbon atoms present in the compounds may be any of R, S and RS.

Preferred salts of the compound of the present invention are hydrochlorides, acetates, sulfates, lactates and the like.

Those compounds of the formula (I) wherein both of $L^1$ and $L^2$ are absent, $A^2$ is —$CH_2$—, X is —NH—, and $R^2$ is phenyl group, naphthyl group or heterocyclic residue, which may have 1 to 3 substituents, are disclosed in WO92/13552 as compounds having platelet aggregation inhibition activity and anticoagulation activity. Therefore, those compounds of the formula (I) wherein both of $L^1$ and $L^2$ are absent, $A^2$ is —$CH_2$—, X is —NH—, and $R^2$ is phenyl group, naphthyl group or heterocyclic residue, which may have 1 to 3 substituents, are excluded from the compounds of the present invention.

The compounds of the present invention have lower platelet aggregation inhibition activity and anticoagulation activity as compared with the compounds disclosed in the above mentioned WO92/13552 and have tumor metastasis inhibition activity, which is not disclosed in WO92/13552.

Further, compounds composed of macromolecular carriers or organic molecules having a definite molecular weight to which a plural number of the amino acid derivatives of the formula (I) are bonded by covalent bonds via connecting groups are encompassed within the scope of the present invention and exhibit the activity like the amino acid derivatives of the formula (I).

Examples of the carrier include phthalic acid, trimesic acid, tetrahydrofurantetracarboxylic acid, polymethacrylic acid, carboxymethyl chitin, sulfated carboxylmethyl chitin, polylysine and chitosan. For example, the amino acid derivatives of the formula (I) can be bonded to carboxyl groups of the carrier by amide bonds through connecting groups such as ethylenediamine and lysine. Further, the derivatives may be bonded to amino groups of polylysine, chitosan and the like directly or through connecting groups such as β-alanine by amide bonds.

The macromolecular carrier, the organic molecule having a definite molecular weight and the connecting group are not limited to those described above.

The compounds of the present invention can be synthesized, for example, by following the steps described below, but not limited thereto.

First Step

An amino acid corresponding to L of which side chain and amino group are protected is condensed with a corresponding $R^1$—X—H, an amino acid corresponding to $L^2$ similarly protected is condensed with a corresponding $R^2$—Y—H and the amino protective groups are removed.

When —X—$R^1$ or —Y—$R^2$ is a hydroxyl group, this step may be carried out by using an amino acid derivative of which side chain and carboxyl terminal group are protected. When —X—$R^1$ or —Y—$R^2$ is —$NH_2$, this step may be carried out by using an amide derivative of a corresponding amino acid.

When $L^1$ and $L^2$ are peptide residues, the above-described process may be carried out by using amino protected amino acids corresponding to the carboxyl terminal residues of the peptide residues and the resultant compound are successively extended by a conventional method using amino acids of which side chains and amino groups are protected to form $L^1$ and $L^2$. When $L^1$ and $L^2$ are absent, this step can be skipped and the condensations of $R^1$—X—H and $R^2$—Y—H may be carried out in the following second step.

Second Step

Arginine of which side chain and amino group are protected and a corresponding $R^1$—X—$L^1$—H are condensed, similarly protected aspartic acid and $R^2$—Y—$L^2$—H are condensed and the amino protective groups are removed.

Third Step

The aspartic acid and the arginine derivatives, of which amino protective groups have been removed in the second step, are successively condensed with a corresponding dicarboxylic acid.

In this step, when $A^1$ or $A^3$ is absent, one of the amino acid derivatives may be reacted with a monohaloalkylcarboxylic acid chloride and then the resultant compound may be condensed with the other amino acid derivative. Preferred monohaloalkylcarboxylic acid chlorides include monobromacetic acid chloride. Otherwise, after a carboxylic acid having an unsaturated group on its end is reacted with one of the amino acid derivatives, the other amino acid derivatives may be condensed with the resultant compound. Preferred carboxylic acids having an unsaturated end include acrylic acid and vinylacetic acid.

Fourth Step

Deprotection and purification.

Fifth Step

Desalification and salt formation

The above steps will be further explained in detail.

With respect to amino acids, protective groups, functional groups and the like, abbreviations according to IUPAC-IUB Commission on Biological Nomenclature and abbreviations conventional in this field will be used in the following explanations and examples.

With respect to amino acid residues, "D-" means D-amino acid residues and "L-" or no indication means L-amino acid residues.

In the first step, the condensation of corresponding protected amino acids and $R^1$—H and the condensation of corresponding protected amino acids and $R^2$—H are carried out by a conventional method using a condensation agent such as the DCC method, the DCC-additive method and the CDI method, esterification using an acid catalyst, reaction with a halide compound in the presence of a base or the like. As the protective group of the protected amino acids, Boc group, Fmoc group, Z group and the like may be used.

Deprotection of the protected amino groups is carried out by TFA, TFA/$CH_2Cl_2$, HCl-dioxane in case of Boc group, by a base such as morpholine in case of Fmoc group, and by hydrolysis in case of Z group. Suitable protective groups can also be selected for protecting side chains taking into consideration the amino protective group and the group connected to the carboxyl terminus.

When —X—$R^1$ or —Y—$R^2$ is a hydroxyl group, benzyl ester group, t-butyl ester group, phenacyl ester group, allyl ester group and the like can be mentioned as suitable carboxyl protective groups. When —X—$R^1$ or —Y—$R^2$ is $NH_2$, amide derivatives of corresponding amino acids can be used.

In the second step, the condensation of protected arginine and $R^1$—$L^1$—H and the condensation of protected aspartic acid and $R^2$—$L^2$—H are carried out by the DCC method, the DCC-additive method and the CDI method or the like.

As the protected arginine, Boc-Arg($NO_2$), Boc-Arg(Z)$_2$, Boc-Arg(Tos) and Boc-Arg(Mts) are particularly useful.

As the protected aspartic acid, Boc-Asp(OBzl) is particularly useful.

Deprotection of the protected amino acid residues may be carried out by TFA, TFA/$CH_2Cl_2$, HCl-dioxane or the like, when Boc protective groups are used.

In the third step, the condensation of the arginine derivative and the aspartic acid derivative with a corresponding dicarboxylic acid are carried out by the DCC method, the DCC-additive method, the CDI method, the DPPA method or the like. The dicarboxylic acid or anhydride thereof may be reacted with one of the amino acid derivatives or the protected peptides to form a half amide compound, which is then reacted with the other amino acid derivative or protected peptides. When a dicarboxylic acid is used, it is preferably used in an amount of 2 to 10 equivalents with an equivalent of one of the amino acid derivatives or the protected peptides. Further, a corresponding dicarboxylic acid dihalide may be reacted with corresponding amino acid derivatives.

When $A^1$ or $A^3$ do not exist, a monochloroalkylcarboxylic acid chloride may be reacted first with one of the amino acid derivatives in dimethylacetamide in the presence of 2 equivalents of potassium carbonate and 1/10 equivalents of potassium iodide and then condensed with the other amino acid derivative.

Alternatively, a carboxylic acid having an unsaturated bond on its terminus may be reacted first with one of the amino acid derivatives in the presence of a base such as triethylamine to obtain a carboxylic acid derivative and then condensed with the other amino acid derivative. For this condensation, conventional condensation methods such as those described above may be used.

The deprotection of the fourth step greatly depends on the protective group used. When benzyl protective groups were used, catalytic hydrogenolysis using Pd or Pt catalyst provided particularly good results. When mesitylene-2-sulfonyl group or tosyl group is used for the guanidino protective groups of arginine, it is preferred to use methanesulfonic acid/thioanisole system or a solution of 1M-trifluoromethanesulfonic acid, thioanisole and m-cresol in trifluoroacetic acid. However, more various means may be used as compared with the kinds of the protective groups used.

Purification method of the obtained compounds according to the present invention may be a usual method for purifying peptides such as recrystallization, gel permeation, column chromatography, thin layer chromatography and liquid chromatography.

The forth step is optional. The desalification and salt formation may be effected easily, in particular, by a method using an ion exchange resin. Purification may be carried out simultaneously with the desalification and salt formation by HPLC or medium-pressure liquid chromatography.

The steric configurations of the asymmetric carbon atoms present in the compounds of the present invention can be selected by using protected amino acids and protected amino acid derivatives having corresponding steric configurations in the first and second steps.

Preferred examples of the compounds according to the present invention are listed below.

$Arg_{rev}$-$COCH_2CO$-Asp,
$Arg_{rev}$-$COCH_2CO$-Asp-Ser,
$Arg_{rev}$-$COCH_2CO$-Asp-Asp,
$Gly_{rev}$-$Arg_{rev}$-$COCH_2CO$-Asp,
$Arg_{rev}$-$Arg_{rev}$-$COCH_2CO$-Asp,
$Gly_{rev}$-$Arg_{rev}$-$COCH_2CO$-Asp-Ser,
$Arg_{rev}$-$Arg_{rev}$-$COCH_2CO$-Asp-Ser,
$Arg_{rev}$-$COCH_2CH_2CO$-Asp,
$Arg_{rev}$-$COCH_2CH_2CO$-Asp-Ser,
$Gly_{rev}$-$Arg_{rev}$-$COCH_2CH_2CO$-Asp,
$Arg_{rev}$-$Arg_{rev}$-$COCH_2CH_2CO$-Asp,
$Gly_{rev}$-$Arg_{rev}$-$COCH_2CH_2CO$-Asp-Ser,
$Arg_{rev}$-$Arg_{rev}$-$COCH_2CH_2CO$-Asp-Ser,
$Arg_{rev}$-$COCH$=$CHCO$-Asp,
$Arg_{rev}$-$COCH$=$CHCO$-Asp-Ser,
$Gly_{rev}$-$Arg_{rev}$-$COCH$=$CHCO$-Asp,
$Arg_{rev}$-$Arg_{rev}$-$COCH$=$CHCO$-Asp,
$Gly_{rev}$-$Arg_{rev}$-$COCH$=$CHCO$-Asp-Ser
$Arg_{rev}$-$Arg_{rev}$-$COCH$=$CHCO$-Asp-Ser,
$Arg_{rev}$-CO-Asp,
$Arg_{rev}$-CO—CO-Asp,
$Arg_{rev}$-$COCH_2$-Asp,
$Arg_{rev}$-$CH_2CO$-Asp,
$Arg_{rev}$-$CH_2CH_2CO$-Asp,
$Arg_{rev}$-$COCH_2CH_2$-Asp In the formulae, "rev" indicates that the amino acid is connected inversely. That is, amino acid residues appended with "rev" have carboxy termini on their left sides and amino termini on their right sides. The carboxyl termini of terminal amino acid residues of the above compounds may be optionally alkylamidated, aralkylamidated or alkyl esterified.

Further examples of the compounds according to the present invention, which include those encompassed within the compounds of the above-described formulae and those not encompassed within them are illustrated below.

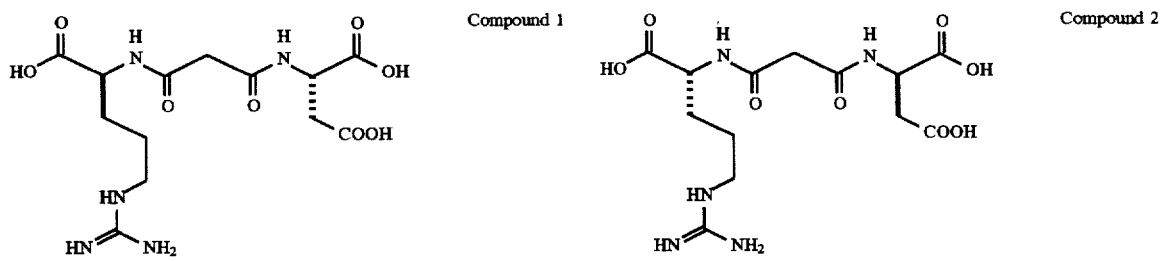

Compound 1

Compound 2

-continued
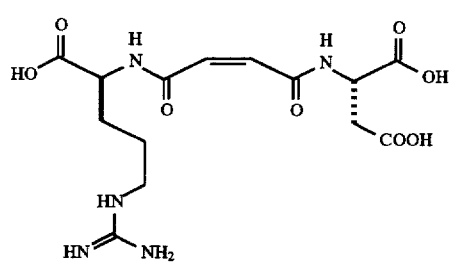
Compound 3
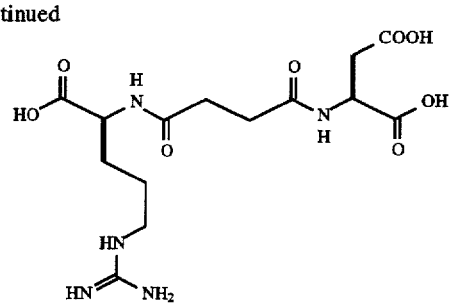
Compound 4
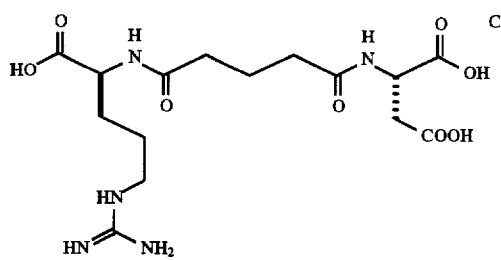
Compound 5
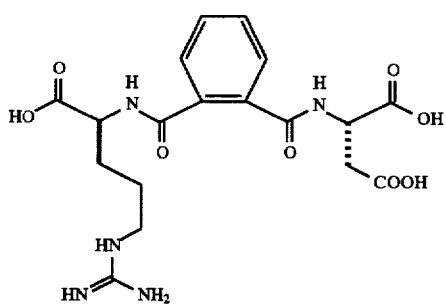
Compound 6
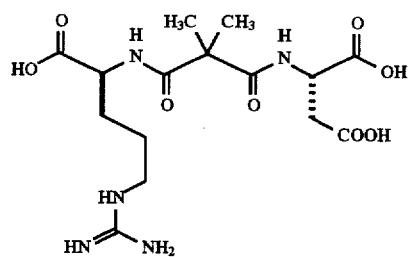
Compound 7
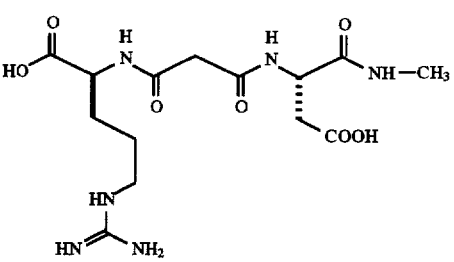
Compound 8
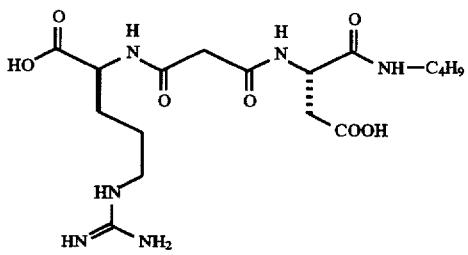
Compound 9
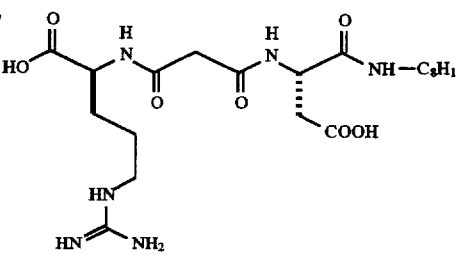
Compound 10
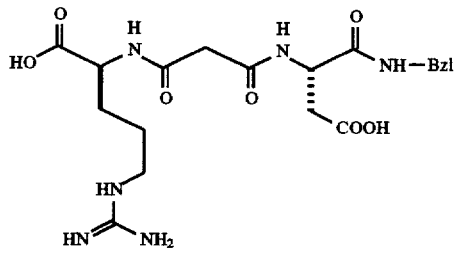
Compound 11
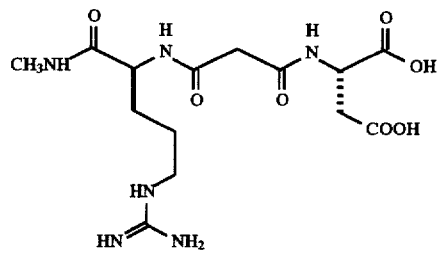
Compound 12
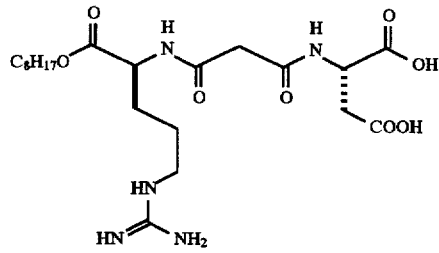
Compound 13
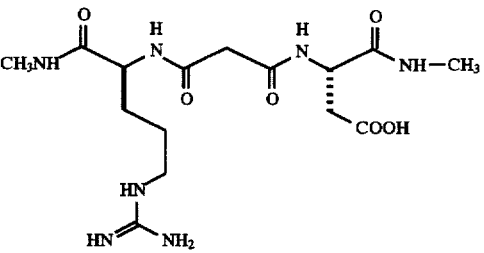
Compound 14

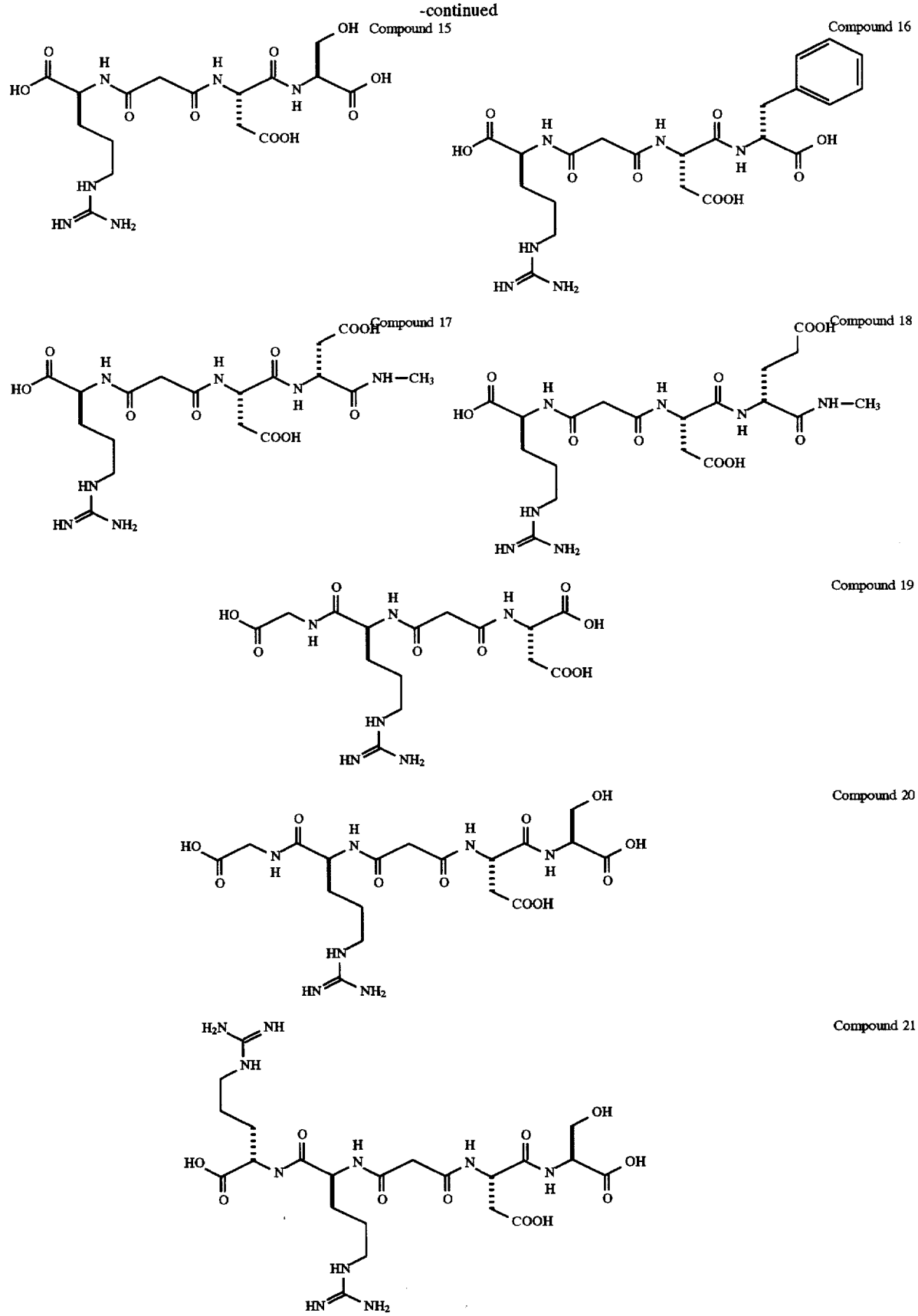

Compound 22
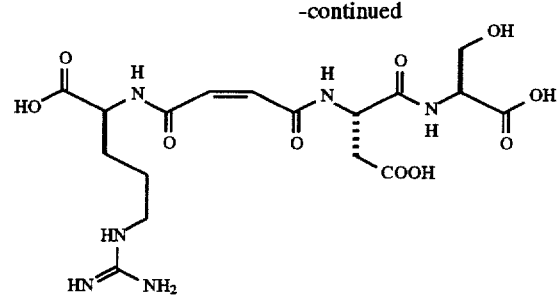
Compound 23
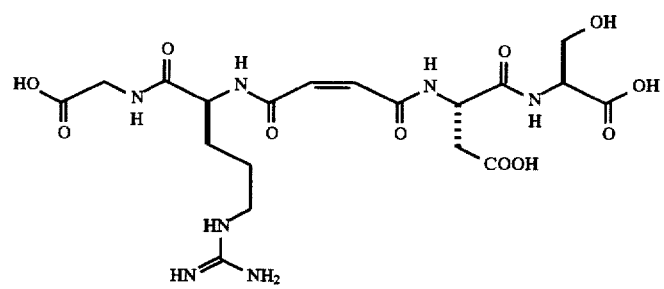
Compound 24
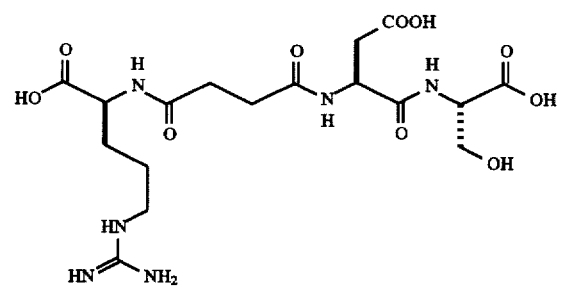
Compound 25
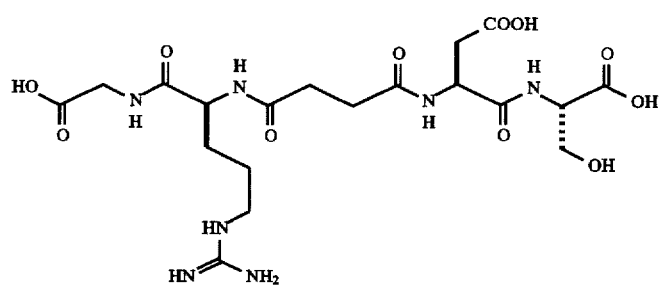
Compound 26
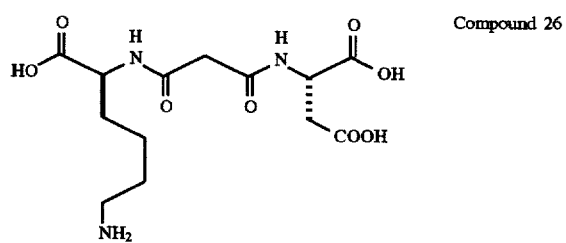
Compound 27
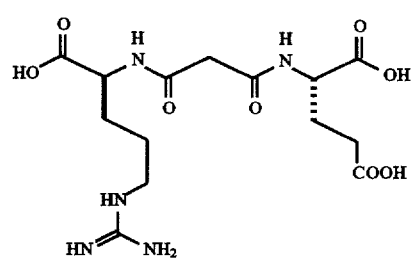
Compound 28
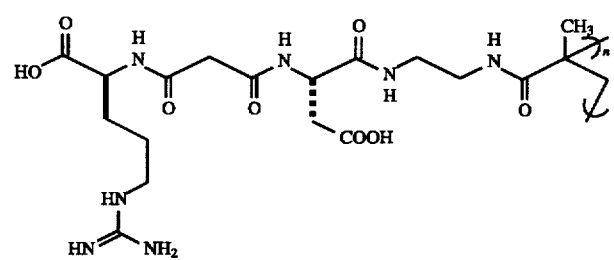

-continued
Compound 29
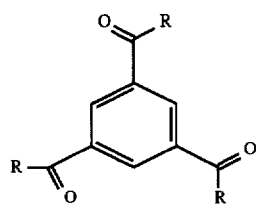
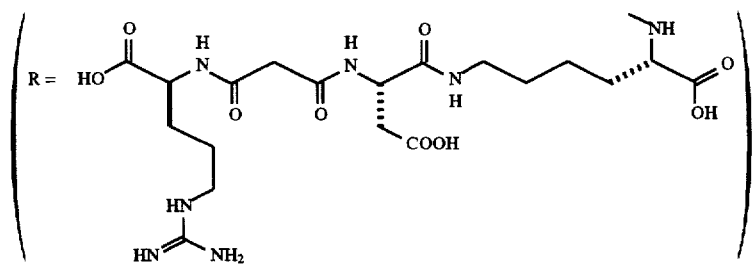
Compound 30
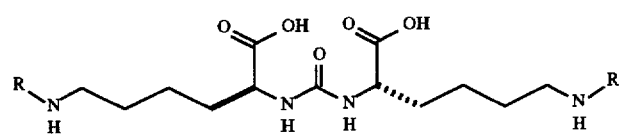
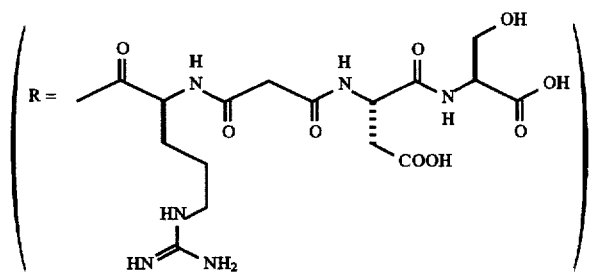
Compound 31
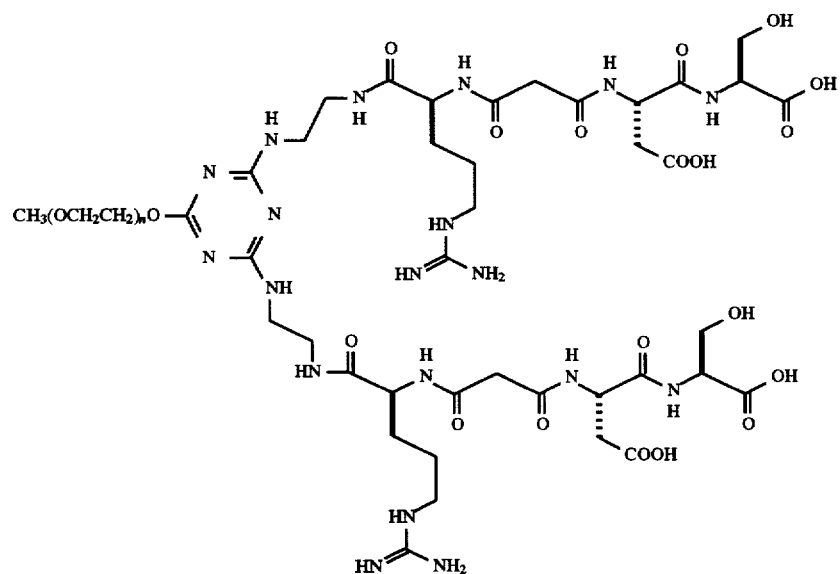

-continued
Compound 32
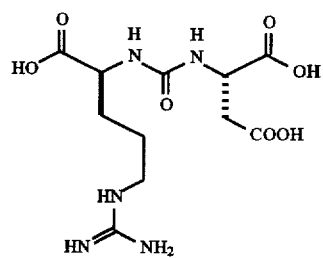
Compound 33
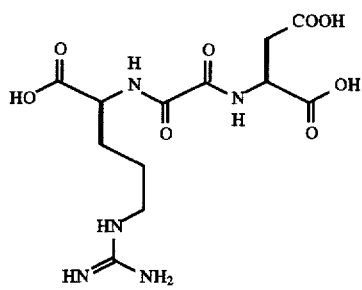
Compound 34
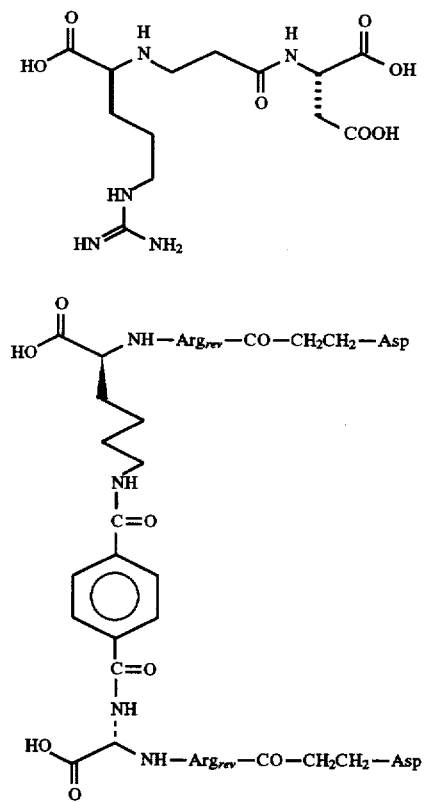
Compound 35
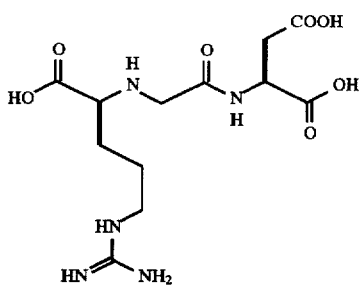
Compound 36
Compound 37
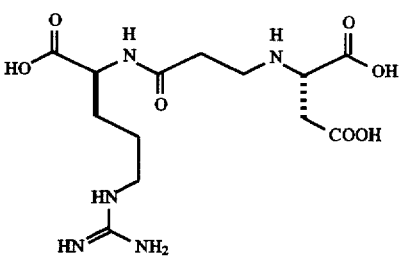
Compound 38
Compound 39
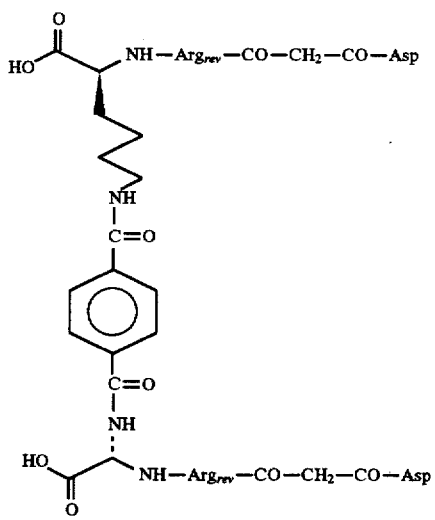

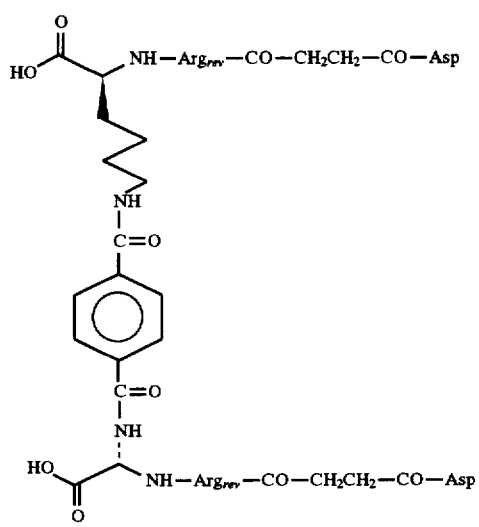

Compound 40

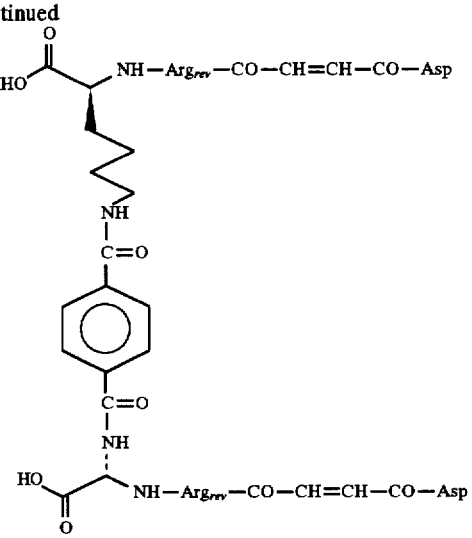

Compound 41

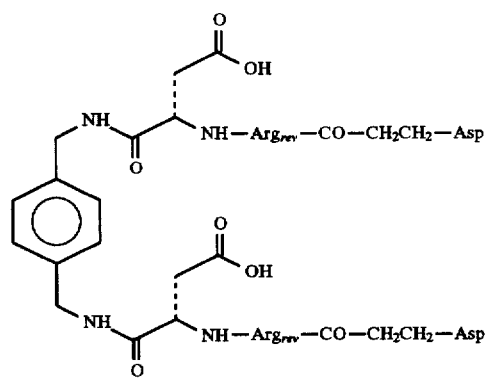

Compound 42

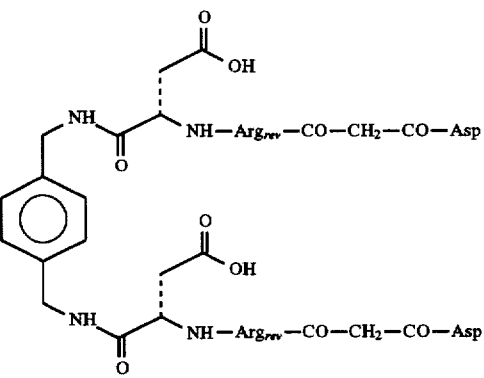

Compound 43

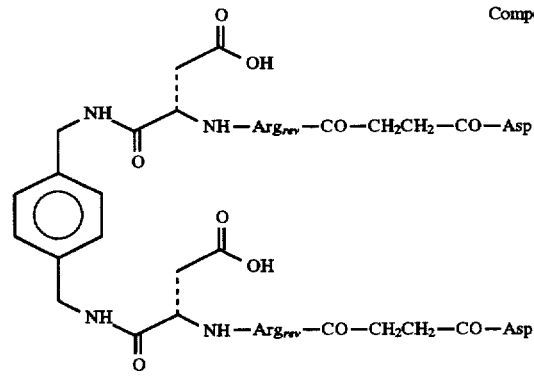

Compound 44

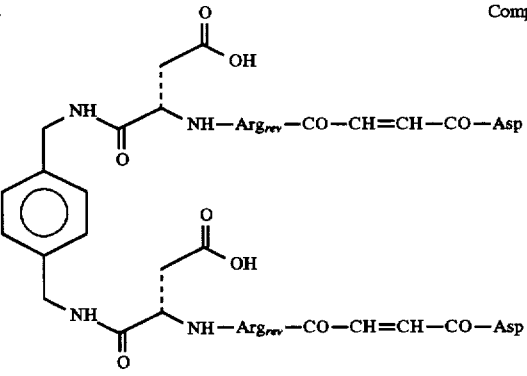

Compound 45

EXAMPLES

Working examples of the preparation of the compounds of the present invention and the determination of their pharmaceutical activities will be shown below, but the present invention is not limited thereto.

Example 1
Synthesis of Compound 1 (acetate)

Malonic acid (1.0 g) and carbonyldiimidazole (3.2 g) were dissolved in chloroform, added with p-toluenesulfonic acid salt of Asp(OBzl)$_2$ (4.9 g), p-toluenesulfonic acid salt of Arg(NO$_2$)OBzl (4.8 g) and diisopropylethylamine (1.3 g) and stirred for 24 hours. The reaction mixture was washed with saturated aqueous solution of sodium hydrogen carbonate and 10% aqueous solution of citric acid and the chloroform layer was dried over anhydrous sodium sulfate. The chloroform was evaporated under reduced pressure and the residue was subjected to silica gel chromatography to collect fractions of chloroform/methanol=9/1, of which solvent was evaporated under reduced pressure to give a protected compound (600 mg).

The obtained protected compound (600 mg) was dissolved in acetic acid (30 ml), added with 10% palladium carbon to carry out hydrogenolysis and catalytic hydrogen reduction under hydrogen atmosphere at 40° C. for 4 days. The reaction solution was filtered through a Celite layer to remove insolubles, the filtrate was concentrated under reduced pressure and the residue was recrystallized from acetic acid/ether to give 30 mg of Compound 1 (acetate)

FAB Mass (M–CH$_3$COO)$^+$ 376

Example 2
Synthesis of Compound 1 (acetate)

Malonic acid (0.82 g) and p-toluenesulfonic acid salt of Asp(OBzl)$_2$ (3.88 g) were dissolved in tetrahydrofuran (20 ml), added with a solution of diphenylphosphorylazide (2.20 g) in tetrahydrofuran (10 ml) under ice cooling, added dropwise with triethylamine (1.64 g) and stirred for 20 minutes.

Then, the reaction mixture was added with Arg(Mts)OBzl hydrochloride (3.86 g) and a solution of diphen ylphosphorylazide (2.2 g) in tetrahydrofuran (10 ml), added dropwise with triethylamine (1.64 g) and stirred for 10 hours. The reaction mixture was concentrated under reduced pressure and the residue was dissolved in ethyl acetate. The organic layer was washed with 10% aqueous solution of citric acid and saturated aqueous solution of sodium hydrogen carbonate and dried over anhydrous sodium sulfate. The ethyl acetate was evaporated under reduced pressure and the residue was subjected to silica gel chromatography to collect ethyl acetate fractions, of which solvent was evaporated under reduced pressure to give a protected compound (1.58 g).

The obtained protected compound (1.5 g) was dissolved in a solution of 1M-trifluoromethanesulfonic acid, thioanisole and m-cresol in trifluoroacetic acid (36 ml) under ice cooling, stirred for 1 hour. Then, the reaction mixture was poured into ether and decantation was carried out. The residue was dissolved in deionized water and the aqueous layer was washed with ether and chloroform and subjected to ion exchange treatment using Amberlite IRA-400 (hydrochloride) to give 360 mg of Compound 1 (hydrochloride)

Purification and trans-salification of the obtained hydrochloride were carried out by subjecting it to liquid chromatography fractionation (ODS, eluent: 0.1% acetic acid) to give 160 mg of Compound 1 (acetate).

FAB Mass (M–CH$_3$COO)$^+$ 376

Elementary analysis (monoacetate) Calcd: H % 5.95; C % 39.72; N % 16.54 Found: H % 5.49; C % 39.59; N % 16.08

$^1$H-NMR (D$_2$O,δ) 1.54–2.08 (m,4H), 2.10 (s,3H,AcOH), 2.86–2.98 (d,2H), 3.16–3.28 (dd,2H), 3.30–3.50 (dd,2H), 4.28–4.48 (dd,1H), 4.60–4.72 (dd,1H)

Example 3
Synthesis of Compound 1 (hydrochloride)

Malonic acid (1.1 g) was dissolved in tetrahydrofuran (10 ml), added with diphenylphosphorylazide (2.8 g) and stirred. Subsequently, the reaction mixture was added dropwise with a suspension of hydrochloride of Arg(Mts)OBzl (2.4 g) and N-methylmorpholine (1.0 g) in tetrahydrofuran (25 ml), stirred for 3 hours, added with N-methylmorpholine (1.5 g) and further stirred for 1 hour. The reaction mixture was concentrated under reduced pressure and the residue was dissolved in ethyl acetate, which was extracted with a saturated aqueous solution of sodium hydrogen carbonate. The aqueous layer, of which pH value was adjusted to 4 with citric acid, was extracted with ethyl acetate and the organic layer was dried over anhydrous sodium sulfate. The ethyl acetate was evaporated under reduced pressure to give malonic acid mono(Nω-trimethylbenzenesulfonyl-L-arginine benzyl ester)amide (1.5 g, yield 60%).

The obtained malonic acid mono(Nω-trimethylbenzenesulfonyl-L-arginine benzyl ester)amide (0.52 g) was dissolved in tetrahydrofuran, added with dicyclohexylcarbodiimide (0.21 g), stirred for 15 minutes under ice cooling, added with p-toluenesulfonic acid salt of Asp (OBzl)$_2$ (0.49 g) and N-methylmorpholine (0.12 g) in tetrahydrofuran/DMF mixture (4 ml) and stirred overnight. The reaction mixture was concentrated under reduced pressure and the residue was dissolved in ethyl acetate. The organic layer was washed with 10% citric acid and saturated aqueous solution of sodium hydrogen carbonate and dried over anhydrous sodium sulfate. The ethyl acetate was evaporated under reduced pressure and residue was subjected to silica gel chromatography to collect fractions of ethyl acetate, of which solvent was evaporated under reduced pressure to give a protected compound (0.68 g, yield: 78%).

The obtained protected compound was dissolved in a solution of 1M-trifluoromethanesulfonic acid, thioanisole and m-cresol in trifluoroacetic acid (20 ml) under ice cooling and stirred for 1 hour. Then, the reaction mixture was poured into ether and decantation was carried out.

The residue was dissolved in deionized water and the aqueous layer was washed with ether and chloroform and subjected to ion exchange treatment using Amberlite IRA-400 (hydrochloride) to give 0.22 mg of Compound 1 (hydrochloride).

FAB Mass (M–Cl)$^+$ 376

Example 4
Synthesis of Compound 2

Malonic acid (11 g) was dissolved in tetrahydrofuran (100 ml), added with diphenylphosphorylazide (15.7 g) and stirred. Subsequently, the reaction mixture was added dropwise with a suspension of hydrochloride of Asp(OBzl)OBzl (20.0 g) and N-methylmorpholine (11.6 g) in tetrahydrofuran (25 ml), stirred for 6 hours, added with N-methylmorpholine (11.6 g) and further stirred for 12 hours. The reaction mixture was concentrated under reduced pressure and the residue was dissolved in ethyl acetate, which was extracted with a saturated aqueous solution of sodium hydrogen carbonate. The aqueous layer, of which pH value was adjusted to 4 with citric acid, was extracted with ethyl acetate and the organic layer was dried over anhydrous sodium sulfate. The ethyl acetate was evaporated under reduced pressure to give malonic acid mono(L-aspartic acid dibenzyl ester)amide (14.0 g).

The obtained malonic acid mono(L-aspartic acid dibenzyl ester)amide (3.99 g) was dissolved in tetrahydrofuran (100 ml), added with diphenylphosphorylazide (2.75 g), stirred for 15 minutes under ice cooling, added with D-Arg(Tos)-OBzl hydrochloride (4.5 g) and N-methylmorpholine (1.00 g) and stirred overnight. The reaction mixture was concentrated under reduced pressure and the residue was dissolved in ethyl acetate. The organic layer was washed with 10% citric acid and saturated aqueous solution of sodium hydrogen carbonate and dried over anhydrous sodium sulfate. The ethyl acetate was evaporated under reduced pressure and the residue was subjected to silica gel chromatography to collect fractions of ethyl acetate, of which solvent was evaporated under reduced pressure to give a protected compound (3.89 g). The obtained protected compound (1.5 g) was dissolved in a solution of 1M-trifluoromethanesulfonic acid, thioanisole and m-cresol in trifluoroacetic acid (40 ml) under ice cooling and stirred for 1 hour. Then, the reaction mixture was poured into ether and decantation was carried out.

The residue was dissolved in deionized water and the aqueous layer was washed with ether and chloroform and subjected to ion exchange treatment using Amberlite IRA-400 (hydrochloride) to give 0.85 mg of Compound 2 (hydrochloride).

Purification and trans-salification of the obtained hydrochloride (200 mg) were carried out by subjecting it to liquid chromatography fractionation (ODS, eluent: 0.1% acetic acid) to give 120 mg of Compound 2 (acetate).

FAB Mass (M–CH$_3$COO)$^+$ 376

Elementary analysis (as monoacetate) Calcd: H % 5.95; C % 39.72; N % 16.54 Found: H % 5.48; C % 40.01; N % 17.00

$^1$H-NMR (D$_2$O,δ) 1.54–2.08 (m,4H), 2.10 (s,3H,AcOH), 2.82–2.98 (d,2H), 3.15–3.28 (dd,2H), 3.40 (s,2H), 4.28–4.48 (dd,1H), 4.60–4.72 (dd,1H)

Example 5
Synthesis of Compound 3 (acetate)

Maleic anhydride (0.98 g) and p-toluenesulfonic acid salt of Asp(OBzl)$_2$ (4.85 g) were dissolved in tetrahydrofuran (20 ml), added with N-methylmorpholine (1.01 g) and stirred for 1 hour.

Subsequently, the reaction mixture was added with dicyclohexylcarbodiimide (2.06 g), Arg(z)$_2$OBzl hydrochloride (4.82 g) and N-methylmorpholine (2.02 g) and stirred overnight. The reaction mixture was concentrated under reduced pressure and the residue was dissolved in ethyl acetate. The organic layer was washed with 10% citric acid and saturated aqueous solution of sodium hydrogen carbonate and dried over anhydrous sodium sulfate. The ethyl acetate was evaporated under reduced pressure and the residue was subjected to silica gel chromatography to collect fractions of chloroform/methanol=95/5, of which solvent was evaporated under reduced pressure to give a protected compound (3.5 g).

The obtained protected compound (0.35 g) was dissolved in a solution of 1M-trifluoromethanesulfonic acid, thioanisole and m-cresol in trifluoroacetic acid (15 ml) under ice cooling and stirred for 1 hour. Then, the reaction mixture was poured into ether and decantation was carried out. The residue was dissolved in deionized water and the aqueous layer was washed with ether and chloroform and subjected to ion exchange treatment using Amberlite IRA-400 (hydrochloride) and treatment with activated carbon and lyophilized to give 26 mg of Compound 3 (hydrochloride).

Purification and trans-salification of the obtained acetate (26 mg) were carried out by subjecting it to liquid chromatography fractionation (ODS, eluent: 5% MeOH containing 0.1% acetic acid) to give 12 mg of Compound 3 (acetate).

FAB Mass (M–CH$_3$COO)$^+$ 388

$^1$H-NMR (D$_2$O,δ) 1.54–2.08 (m,4H), 2.10 (s,3H,ACOH), 2.82–2.92(d, 2H), 3.18–3.28 (dd,2H), 4.28–4.40 (m,1H), 4.60–4.72 (dd,1H), 6.30–6.38 (d,1H), 6.36–6.46 (d,1H)

Example 6
Synthesis of Compound 4 (acetate)

The title compound was synthesized in the same manner as in Example 5 by using succinic anhydride. Liquid chromatography fractionation was carried out under the conditions of ODS, 5% MeOH (containing 0.1% acetic acid).

FAB Mass (M–CH$_3$COO)$^+$ 390

$^1$H-NMR (D$_2$O,δ) 1.58–2.08 (m,4H), 2.10 (s,3H,AcOH), 2.62 (br s, 4H), 2.82–2.92 (d,2H), 3.18–3.28 (dd,2H), 4.28–4.40 (dd,1H), 4.60–4.72 (dd,1H)

Example 7
Synthesis of Compound 5 (acetate)

The title compound was synthesized in the same manner as in Example 5 by using glutaric anhydride. Liquid chromatography fractionation was carried out under the conditions of ODS, 10% MeOH (containing 0.1% acetic acid).

FAB Mass (M–CH$_3$COO)$^+$ 404

$^1$H-NMR (D$_2$O,δ) 1.58–2.08 (m+t,6H), 2.10 (s,3H, AcOH), 2.28–2.40 (t,4H), 2.82–2.92 (d,2H), 3.18–3.28 (dd, 2H), 4.22–4.34 (m,1H), 4.60–4.78 (dd,1H)

Example 8
Synthesis of Compound 6 (acetate)

The title compound was synthesized in the same manner as in Example 5 by using phthalic anhydride. Liquid chromatography fractionation was carried out under the conditions of ODS, 20% MeOH (containing 0.1% acetic acid).

FAB Mass (M–CH$_3$COO)$^+$ 438

$^1$H-NMR (D$_2$O,δ) 1.58–2.08 (m,4H), 2.10 (s,3H,AcOH), 2.82–2.92 (d,2H), 3.20–3.28 (dd,2H), 4.22–4.34 (m,1H), 4.70–4.78 (dd,1H), 7.64 (s,4H)

Example 9
Synthesis of Compound 7 (acetate)

Dimethylmalonic acid (264 mg) and diphenylphosphorylazide (1.10 g) were dissolved in dimethylformamide (10 ml) and stirred. Subsequently, the solution was added with p-toluenesulfonic acid salt of Asp(OBzl)$_2$ (970 mg), added dropwise with triethylamine (0.40 g) and stirred for 1 hour.

Then, the solution was added with Arg(Z)$_2$OBzl hydrochloride (1.13 g), added dropwise with triethylamine (0.40 g) and stirred overnight. The reaction mixture was concentrated under reduced pressure and the residue was dissolved in ethyl acetate. The organic layer was washed with 10% aqueous solution of citric acid and saturated aqueous solution of sodium hydrogen carbonate and dried over anhydrous sodium sulfate. The ethyl acetate was evaporated under reduced pressure and the residue was subjected to silica gel chromatography to collect fractions of hexane/ethyl acetate=8/2, of which solvent was evaporated under reduced pressure to give a protected compound (319 mg).

The obtained protected compound (300 mg) was dissolved in a solution of 1M-trifluoromethanesulfonic acid, thioanisole and m-cresol in trifluoroacetic acid (8 ml) under ice cooling and stirred for 1 hour. Then, the reaction mixture was poured into ether and decantation was carried out. The residue was dissolved in deionized water, subjected to ion exchange treatment using Amberlite IRA-400 (hydrochloride) and treatment with activated carbon and lyophilized to give 25 mg of Compound 7 (hydrochloride).

Purification and trans-salification of the obtained hydrochloride were carried out by subjecting it to liquid chromatography fractionation (ODS, eluent: 10% MeOH containing 0.1% acetic acid) to give 11 mg of Compound 7 (acetate).

FAB Mass (M–CH$_3$COO)$^+$ 404

$^1$H-NMR (D$_2$O,δ) 1.48–1.50 (d,6H), 1.58–2.14 (m,4H), 2.10 (s,3H, ACOH), 2.82–2.92 (d,2H), 3.18–3.28 (dd,2H), 4.22–4.40 (m,1H), 4.58–4.68 (dd,1H)

Example 10
Synthesis of Asp(OBzl)-NHMe hydrochloride

Boc-Asp(OBzl) (6.4 g) was dissolved in tetrahydrofuran (30 ml), added with dicyclohexylcarbodiimide (4.1 g), hydroxybenzotriazole (3.0 g), methylamine hydrochloride (2.0 g) and diisopropylethylamine (3.9 g) under ice cooling and stirred for 10 hours. Insolubles were removed from the mixture by filtration and the filtrate was concentrated under reduced pressure. The residue was dissolved in ethyl acetate and the organic layer was washed with 10% aqueous solution of citric acid and saturated aqueous solution of sodium hydrogen carbonate and dried over anhydrous sodium sulfate. Then the ethyl acetate was evaporated under reduced pressure. The residue was recrystallized from ethyl acetate/hexane to give Boc-Asp(OBzl)-NHMe (3.9 g).

Boc-Asp(OBzl)-NHMe (3.9 g) was dissolved in dioxane (20 ml), added with 4M-HCl dioxane solution (20 ml) and stirred for 1 hour at room temperature. The reaction mixture was evaporated under reduced pressure and the residue was crystallized from ether to quantitatively give Asp(OBzl)-NHMe hydrochloride.

In a similar manner, Asp(OBzl)-NHC$_4$H$_9$, Asp(OBzl)-NHC$_8$H$_{17}$, Asp(OBzl)-NHBzl and the like were synthesized.

Example 11
Synthesis of Arg(Mts)-NHMe hydrochloride

Boc-Arg(Mts) (13.7 g) was dissolved in tetrahydrofuran (100 ml), added with dicyclohexylcarbodiimide (6.2 g), hydroxybenzotriazole (4.6 g), methylamine hydrochloride (3.0 g) and diisopropylethylamine (5.8) under ice cooling and stirred for 15 hours. Insolubles were removed from the mixture by filtration and the filtrate was concentrated under reduced pressure. The residue was dissolved in ethyl acetate and the organic layer was washed with 10% aqueous solution of citric acid and saturated aqueous solution of sodium hydrogen carbonate and dried over anhydrous sodium sulfate. Then, the ethyl acetate was evaporated under reduced pressure.

The residue was dissolved in dioxane (20 ml), added with 4M-HCl dioxane solution (20 ml) and stirred for 1 hour at room temperature. The reaction mixture was evaporated under reduced pressure and the residue was crystallized from ether to give Arg(Mts)-NHMe hydrochloride (13.6 g).

Example 12
Synthesis of Arg(Z)$_2$—OC$_8$H$_{17}$ hydrochloride

Boc-Arg(Z)$_2$ (5.5 g) was dissolved in tetrahydrofuran (100 ml), added with dicyclohexylcarbodiimide (2.1 g), octanol (1.3 g) and diisopropylethylamine (1.3 g) under ice cooling and stirred for 24 hours. Insolubles were removed from the mixture by filtration and the filtrate was concentrated under reduced pressure. The residue was dissolved in ethyl acetate and the organic layer was washed with 10% aqueous solution of citric acid and saturated aqueous solution of sodium hydrogen carbonate and dried over anhydrous sodium sulfate. Then, the ethyl acetate was evaporated under reduced pressure.

The residue was dissolved in dioxane (20 ml), added with 4M-HCl dioxane solution (20 ml) and stirred for 1 hour at room temperature. The reaction mixture was evaporated under reduced pressure and the residue was crystallized from ether to give Arg(Z)$_2$—OC$_8$H$_{17}$ hydrochloride (2.6 g).

Example 13
Synthesis of Compound 8 (acetate)

Malonic acid (0.38 g) and Asp(OBzl)-NHMe hydrochloride (0.95 g) were dissolved in dimethylformamide (5 ml), added with solution of diphenylphosphorylazide (0.97 g) and triethylamine (0.71 g) in tetrahydrofuran under ice cooling and stirred for 20 minutes.

Then, the mixture was added with Arg(Z)$_2$OBzl hydrochloride (1.99 g) and solution of diphenylphosphorylazide (0.97 g) and triethylamine (0.71 g) in tetrahydrofuran (2 ml) and stirred overnight. The reaction mixture was concentrated under reduced pressure and the residue was dissolved in ethyl acetate and the organic layer was washed with 10% aqueous solution of citric acid and saturated aqueous solution of sodium hydrogen carbonate and dried over anhydrous sodium sulfate. The ethyl acetate was evaporated under reduced pressure and the residue was subjected to silica gel chromatography to collect fractions of chloroform/methanol=95/5, of which solvent was evaporated under reduced pressure to give a protected compound (0.25 g).

The protected compound (0.25 g) was dissolved in a solution of 1M-trifluoromethanesulfonic acid, thioanisole and m-cresol in trifluoroacetic acid (5 ml) under ice cooling and stirred for 1 hour. Then, the reaction mixture was poured into ether and decantation was carried out. The residue was dissolved in deionized water and subjected to ion exchange treatment using Amberlite IRA-400 (hydrochloride) and treatment with activated carbon and lyophilized to give 90 mg of Compound 8 (hydrochloride).

Purification and trans-salification of the obtained acetate (26 mg) were carried out by subjecting it to liquid chromatography fractionation (ODS, eluent: 0.1% acetic acid) to give 11 mg of Compound 8 (acetate).

FAB Mass (M—CH$_3$COO)$^+$ 389

$^1$H-NMR (D$_2$O,δ) 1.58–2.14 (m,4H), 2.10 (s,3H,AcOH), 2.72 (s,3H), 2.82–2.92 (d,2H), 3.18–3.28 (dd,2H), 3.40 (s,2H), 4.22–4.40 (m,1H), 4.54–4.68 (dd, 1H)

Example 14
Synthesis of Compound 9 (hydrochloride)

Malonic acid (0.78 g) and diphenylphosphorylazide (4.13 g) were dissolved in tetrahydrofuran (10 ml) and added dropwise with a suspension of Asp(OBzl)-NHC$_4$H$_9$ hydrochloride (2.34 g) and N-methylmorpholine (2.27 g) over 4 hours. After stirring for 4 hours, the mixture was added with Arg(Mts)-OBzl hydrochloride (3.61 g) and N-methylmorpholine (0.75 g), stirred for 2 hours, added with diphenylphosphorylazide (2.07 g) and N-methylmorpholine (0.75 g) and stirred for twenty four hours.

The reaction mixture was evaporated under reduced pressure and the residue was dissolved in ethyl acetate and washed with 10% aqueous solution of citric acid and saturated aqueous solution of sodium hydrogen carbonate. The organic layer was dried over anhydrous sodium sulfate and the ethyl acetate was evaporated under reduced pressure. The residue was subjected to silica gel chromatography to collect fractions of chloroform/methanol=9/1, of which solvent was evaporated under reduced pressure to give a protected compound (0.48 g).

The protected compound (0.65 g) was dissolved in a solution of 1M-trifluoromethanesulfonic acid, thioanisole and m-cresol in trifluoroacetic acid (24 ml) under ice cooling and stirred for 1 hour. Then, the reaction mixture was poured into ether and decantation was carried out. The residue was dissolved in deionized water and subjected to ion exchange treatment using Amberlite IRA-400 (hydrochloride) and treatment with activated carbon and lyophilized to give 90 mg of Compound 9 (hydrochloride).

FAB Mass (M—Cl)$^+$ 431

$^1$H-NMR (D$_2$O,δ) 0.88 (t,3H), 1.28 (m,2H), 1.38–2.14 (m,6H), 2.80–2.90 (2H), 3.20–3.28 (2H), 3.40–3.52 (4H), 4.22–4.40 (1H), 4.54–4.68 (1H)

Example 15
Synthesis of compound 10 (hydrochloride)

The title compound was synthesized in the same manner as Example 14 by using Asp(OBzl)-NHC$_8$H$_{17}$ hydrochloride.

FAB Mass (M—Cl)$^+$ 487

$^1$H-NMR (CDCl$_3$+D$_2$O,δ) 0.88(t,3H), 1.28 (s,10H), 1.38–2.14 (m,6H), 2.90–3.00 (2H), 3.16–3.29 (2H), 3.40–3.52 (4H), 4.28–4.51 (1H)

Example 16
Synthesis of Compound 11 (hydrochloride)

The title compound was synthesized in the same manner as Example 14 by using Asp(OBzl)-NH-Bzl hydrochloride.

FAB Mass (M—Cl)$^+$ 465

$^1$H-NMR (D$_2$O,δ) 1.54–2.08 (m,4H), 2.10 (s,3H,AcOH), 2.82–2.98(d, 2H), 3.15–3.28 (dd,2H), 3.40 (s,2H), 4.28–4.48 (dd,1H), 4.60–4.72 (dd,1H), 7.36 (s,5H)

Example 17
Synthesis of Compound 12 (acetate)

Malonic acid (0.82 g), p-toluenesulfonic acid salt of Asp(OBzl) (3.9 g) was dissolved in dimethylformamide (20 ml), added with diphenylphosphorylazide (2.2 g) and triethylamine (1.6 g) under ice cooling and stirred for 20 minutes.

Then, the mixture was added with Arg(Mts)-NHMe hydrochloride (2.7 g) and then with diphenylphosphorylazide (2.2 g) and triethylamine (1.6 g) and stirred overnight. The reaction mixture was concentrated under reduced pressure and the residue was dissolved in ethyl acetate. The organic layer was washed with 10% aqueous solution of citric acid and saturated aqueous solution of sodium hydrogen carbonate and dried over anhydrous sodium sulfate. The ethyl acetate was evaporated under reduced pressure and the residue was subjected to silica gel chromatography to collect fractions of chloroform/methanol=95/5, of which solvent was evaporated under reduced pressure to give a protected compound (0.82 g).

The protected compound (0.30 g) was dissolved in a solution of 1M-trifluoromethanesulfonic acid, thioanisole and m-cresol in trifluoroacetic acid (5 ml) under ice cooling and stirred for 1 hour. Then, the reaction mixture was poured into ether and decantation was carried out. The residue was dissolved in deionized water and subjected to ion exchange treatment using Amberlite IRA-400 (hydrochloride) and treatment with activated carbon and lyophilized to give 100 mg of Compound 12 (hydrochloride).

Purification and trans-salification of the obtained hydrochloride were carried out by subjecting it to liquid chromatography fractionation (ODS, eluent: 0.1% acetic acid) to give 45 mg of Compound 12 (acetate).

FAB Mass $(M-CH_3COO)^+$ 389

$^1$H-NMR $(D_2O,\delta)$ 1.58–2.14 (m,4H), 2.10 (s,3H,AcOH), 2.72 (s,3H), 2.82–2.98 (d,2H), 3.12–3.28 (dd,2H), 3.40 (s,2H), 4.22–4.40 (m,1H), 4.70–4.88

Example 18
Synthesis of Compound 13 (acetate)

Malonic acid (1.0 g) and dicyclohexylcarbodiimide (2.1 g) were dissolved in chloroform, added with p-toluenesulfonic acid salt of Asp(OBzl)$_2$ (4.9 g), trifluoroacetic acid salt of Arg(Z)$_2$OC$_8$H$_{17}$ (6.7 g) and diisopropylethylamine (1.3 g) and stirred twenty four hours. The reaction mixture was washed with 10% aqueous solution of citric acid and saturated aqueous solution of sodium hydrogen carbonate and the chloroform layer was dried over anhydrous sodium sulfate. The chloroform was evaporated under reduced pressure and the residue was subjected to silica gel chromatography to collect fractions of chloroform/methanol=9/1, of which solvent was evaporated under reduced pressure to give a protected compound (420 mg).

The obtained protected compound (400 mg) was dissolved in acetic acid (30 ml) and added with 10% palladium carbon and hydrogenolysis was carried out at 40° C. for 2 days under hydrogen atmosphere. The reaction mixture was filtered through a Celite layer to remove insolubles and the filtrate was concentrated under reduced pressure. The residue was recrystallized from acetic acid/ether to give 120 mg of Compound 13 (acetate).

FAB Mass $(M-Cl)^+$ 488

$^1$H-NMR $(CDCl_3+D_2O,\delta)$ 0.88 (t,3H), 1.28 (s,10H), 1.38–2.14 (m,6H), 2.90–3.00 (2H), 3.16–3.29 (2H), 3.36–3.50 (4H), 4.12–4.51 (2H)

Example 19
Synthesis of Compound 14 (acetate)

Malonic acid (0.73 g) and Asp(OBzl)-NHMe hydrochloride (1.90 g) were dissolved in dimethylformamide (20 ml), added with diphenylphosphorylazide (1.93 g) and triethylamine (1.42 g) under ice cooling and stirred for 20 minutes.

Then, the mixture was added with Arg(Mts)-NHMe hydrochloride (2.4 g) and then with diphenylphosphorylazide (1.93 g) and triethylamine (0.71 g) and stirred overnight. The reaction mixture was concentrated under reduced pressure and the residue was dissolved in ethyl acetate. The organic layer was washed with 10% aqueous solution of citric acid and saturated aqueous solution of sodium hydrogen carbonate and dried over anhydrous sodium sulfate. The ethyl acetate was evaporated under reduced pressure and the residue was subjected to silica gel chromatography to fractions of collect ethyl acetate/methanol=85/15. The solvent of the fractions was evaporated under reduced pressure and the residue was again subjected to silica gel chromatography to collect fractions of ethyl chloroform/methanol=8/2. The solvent of the fractions was evaporated under reduced pressure and the residue was recrystallized from methanol/ether and acetonitrile/ether to give a protected compound (0.36 g).

The protected compound (0.35 g) was dissolved in a solution of 1M-trifluoromethanesulfonic acid, thioanisole and m-cresol in trifluoroacetic acid (2.6 ml) with ice cooling and stirred for 1 hour. Then, the reaction mixture was poured into ether and decantation was carried out. The residue was dissolved in deionized water and subjected to ion exchange treatment using Amberlite IRA-400 (hydrochloride) and treatment with activated carbon and lyophilized to give 52 mg of Compound 14 (hydrochloride).

The obtained hydrochloride was purified by liquid chromatography fractionation (ODS, eluent: 0.1% acetic acid) to give 28 mg of Compound 14 (acetate).

FAB Mass $(M-CH_3COO)^+$ 402

$^1$H-NMR $(D_2O,\delta)$ 1.50–2.04 (m,4H), 2.10 (s,3H,AcOH), 2.70–2.88 (dd+s,8H), 3.16–3.24 (dd,2H), 3.40 (s,2H), 4.22–4.40 (dd,1H), 4.60–4.68 (dd,1H)

Example 20
Synthesis of Asp(OBzl)-Ser(Bzl)-OBzl hydrochloride

Boc-Asp(OBzl) (25.2 g) was dissolved in tetrahydrofuran (400 ml), added with dicyclohexylcarbodiimide (17.7 g), hydroxybenzotriazole (11.93 g), Ser(Bzl)-OBzl hydrochloride (31.1 g) and diisopropylethylamine (10.1 g) with ice cooling and stirred for 24 hours. Insolubles were removed from the mixture by filtration and the filtrate was concentrated under reduced pressure. The residue was dissolved in ethyl acetate and the organic layer was washed with 10% aqueous solution of citric acid and saturated aqueous solution of sodium hydrogen carbonate and dried over anhydrous sodium sulfate. Then, the ethyl acetate was evaporated under reduced pressure.

The residue was subjected to silica gel chromatography to collect fractions of hexane/ethyl acetate=7/3 to obtain Boc-Asp(OBzl)-Ser(Bzl)-OBzl (42.1 g).

Boc-Asp(OBzl)-Ser(Bzl)-OBzl (42.1 g) was dissolved in dioxane (100 ml), added with a solution of 4M-HCl/dioxane (150 ml) and stirred for 1 hour at room temperature. The reaction mixture was evaporated under reduced pressure and the residue was crystallized from ether to give Asp(OBzl)-Ser(Bzl)-OBzl hydrochloride (33.7 g).

Similarly, by using dicyclohexylcarbodiimide as a condensing agent, Asp(OBzl)-D-Phe-OBzl hydrochloride, Asp(OBzl)-D-Glu-NHMe hydrochloride, Asp(OBzl)-D-Asp-OBzl hydrochloride, Arg(Mts)-Arg(Mts)-OBzl hydrochloride and Arg(Mts)-Gly-OBzl hydrochloride were prepared.

Example 21
Synthesis of Compound 15 (acetate)

Malonic acid (4.16 g) and hydroxybenzotriazole (1.53 g) were dissolved in tetrahydrofuran (150 ml) and added with dicyclohexylcarbodiimide (2.47 g) with stirring and ice cooling. After stirring for 30 minutes, the mixture was added dropwise with a suspension of Asp(OBzl)-Ser(Bzl)-OBzl hydrochloride (5.25 g) and N-methylmorpholine (2.02 g) in tetrahydrofuran (100 ml) over 1.5 hours. After completion of the addition, the mixture was further added with dicyclohexylcarbodiimide (0.52 g) and stirred overnight. After removing insolubles, the solvent was evaporated under reduced pressure. The residue was dissolved in ethyl acetate and the organic layer was washed with 10% aqueous solution of citric acid and deionized water and dried over anhydrous sodium sulfate. The ethyl acetate was evaporated under reduced pressure, the residue was dissolved in toluene and the toluene was evaporated under reduced pressure. The residue was dissolved in tetrahydrofuran, added with dicyclohexylcarbodiimide (2.06 g), hydroxybenzotriazole (1.53 g), Arg(Mts)-OBzl hydrochloride (4.83 g) and N-methylmorpholine (2.02 g) and stirred overnight. Insolubles were removed by filtration and the filtrate was evaporated under reduced pressure. The residue was dissolved in ethyl acetate and the organic layer was washed with 10% aqueous solution of citric acid and saturated aqueous solution of sodium hydrogen carbonate and dried over anhydrous sodium sulfate. The ethyl acetate was evaporated under reduced pressure and the residue was subjected to silica gel chromatography to collect ethyl acetate fractions. The solvent of the fractions was evaporated under reduced pressure to give a protected compound (3.1 g).

The protected compound (1.5 g) was dissolved in a solution of 1M-trifluoromethanesulfonic acid, thioanisole and m-cresol in trifluoroacetic acid (36 ml) with ice cooling and stirred for 1 hour. Then, the reaction mixture was poured into ether and decantation was carried out. The residue was dissolved in deionized water and the aqueous layer was washed with ether and chloroform and subjected to ion exchange treatment using Amberlite IRA-400 (hydrochloride) to give 220 mg of Compound 15 (hydrochloride).

Purification and trans-salification of the obtained hydrochloride were carried out by subjecting it to liquid chromatography fractionation (ODS, eluent: 0.1% acetic acid) to give 120 mg of Compound 15 (acetate).

FAB Mass $(M-CH_3COO)^+$ 463

$^1$H-NMR $(D_2O, \delta)$ 1.54–2.08 (m,4H), 2.10 (s,3H,AcOH), 2.82–2.94 (dd,2H), 3.15–3.28 (dd,2H), 3.34–3.56 (dd,2H), 3.90–3.94 (dd,2H), 4.28–4.36 (dd, 1H), 4.36–4.44 (dd,1H)

Example 22
Synthesis of Compound 16 (acetate)

The title compound was synthesized in the same manner as Example 15 by using Asp(OBzl)-D-Phe-OBzl hydrochloride.

Chloroform/methanol=97.5/2.5 was used as the eluent for the silica gel chromatography purification of the protected compound and 3% MeOH containing 0.1% acetic acid was used as the eluent for the liquid chromatography fractionation and purification of the final product.

FAB Mass $(M-CH_3COO)^+$ 523

$^1$H-NMR $(D_2O, \delta)$ 1.54–2.08 (m,4H), 2.10 (s,3H,AcOH), 2.62–2.70 (dd,2H), 2.90–3.38 (ddd,2H), 3.15–3.28 (dd,2H), 3.38–3.48 (dd,2H), 4.28–4.36 (dd,1H), 4.56–4.68 (dd,1H)

Example 23
Synthesis of compound 17 (acetate)

The title compound was synthesized in the same manner as Example 15 by using Asp(OBzl)-D-Asp(OBzl)-NHMe hydrochloride.

Chloroform/methanol=95/5 was used as the eluent for the silica gel chromatography purification of the protected compound and 3% MeOH containing 0.1% acetic acid was used as the eluent for the liquid chromatography fractionation and purification of the final product.

FAB Mass $(M-CH_3COO)^+$ 504

$^1$H-NMR $(D_2O, \delta)$ 1.58–2.04 (m,4H), 2.10 (s,3H,AcOH), 2.72 (s,3H), 2.80–2.94 (dd,4H), 3.15–3.28 (dd,2H), 3.32–3.54 (dd,2H), 4.28–4.36 (dd,2H)

Example 24
Synthesis of Compound 18 (acetate)

The title compound was synthesized in the same manner as Example 23 by using Asp(OBzl)-D-Glu(OBzl)-NHMe hydrochloride.

Chloroform/methanol=95/5 was used as the eluent for the silica gel chromatography purification of the protected compound and 5% MeOH containing 0.1% acetic acid was used as the eluent for the liquid chromatography fractionation and purification of the final product.

FAB Mass $(M-CH_3COO)^+$ 518

$^1$H-NMR $(D_2O, \delta)$ 1.58–2.04 (m,4H), 2.10 (s,3H,AcOH), 2.42–2.50 (dd,2H), 2.54–2.78 (dd+s,5H), 2.80–2.90 (dd, 2H), 3.15–3.28 (dd,2H), 3.38–3.44 (d,2), 4.22–4.36 (m,2H), 4.60–4.68 (dd,1H)

Example 25
Synthesis of Compound 19 (acetate)

Malonic acid (4.16 g) and hydroxybenzotriazole (1.53 g) were dissolved in tetrahydrofuran (150 ml) and added with dicyclohexylcarbodiimide (2.47 g) with stirring and ice cooling. After stirring for 30 minutes, the mixture was added dropwise with a suspension of p-toluenesulfonic acid salt of Asp(OBzl)-OBzl (4.85 g) and N-methylmorpholine (2.02 g) in tetrahydrofuran (100 ml) over 1.5 hours. After completion of the addition, the mixture was further added with dicyclohexylcarbodiimide (0.52 g) and stirred overnight. After removing insolubles, the solvent was evaporated under reduced pressure. The residue was dissolved in ethyl acetate and the organic layer was washed with 10% aqueous solution of citric acid and deionized water and dried over anhydrous sodium sulfate. The ethyl acetate was evaporated under reduced pressure. Then, the residue was dissolved in toluene and the toluene was evaporated under reduced pressure. The residue was dissolved in tetrahydrofuran, added with dicyclohexylcarbodiimide (2.06 g), hydroxybenzotriazole (1.53 g), Arg(Mts)-Gly-OBzl hydrochloride (5.39 g), N-methylmorpholine (2.02 g) and stirred overnight. Insolubles were removed by filtration and the filtrate was evaporated under reduced pressure. The residue was dissolved in ethyl acetate and the organic layer was washed with 10% aqueous solution of citric acid and saturated aqueous solution of sodium hydrogen carbonate and dried over anhydrous sodium sulfate. The ethyl acetate was evaporated under reduced pressure and the residue was subjected to silica gel chromatography to collect fractions of chloroform/methanol=95/5. The solvent of the fractions was evaporated under reduced pressure to give a protected compound (2.33 g).

The obtained protected compound (2.00 g) was dissolved in a solution of 1M-trifluoromethanesulfonic acid, thioanisole and m-cresol in trifluoroacetic acid (45 ml) with ice cooling and stirred for 1 hour. Then, the reaction mixture was poured into ether and decantation was carried out. The residue was dissolved in deionized water and the aqueous layer was washed with ether and chloroform and subjected to ion exchange treatment using Amberlite IRA-400 (hydrochloride) to give 450 mg of Compound 19 (hydrochloride).

Purification and trans-salification of the obtained hydrochloride were carried out by subjecting it to liquid chromatography fractionation (ODS, eluent: 10% MeOH containing 0.1% acetic acid) to give 170 mg of Compound 19 (acetate).

FAB Mass $(M-CH_3COO)^+$ 433

$^1$H-NMR$_2$(D$_2$O,$\delta$) 1.54–2.08 (m,4H), 2.10 (s,3H,AcOH), 2.86–2.98 (d,2H), 3.16–3.28 (m,2H), 3.30–3.50 (d,2H), 3.98 (s,2H), 4.28–4.48 (m,1H), 4.60–4.72 (m,1H)

Example 26
Synthesis of Compound 20 (acetate)

The title compound was synthesized in the same manner as Example 25 by using Asp(OBzl)-Ser(Bzl)-OBzl hydrochloride and Arg(Mts)-Gly-OBzl hydrochloride.

Chloroform/methanol=95/5 was used as the eluent for the silica gel chromatography purification of the protected compound and 10% MeOH containing 0.1% acetic acid was used as the eluent for the liquid chromatography fractionation and purification of the final product.

FAB Mass $(M-CH_3COO)^+$ 520

$^1$H-NMR$_2$ (D$_2$O,$\delta$) 1.54–2.08 (m,4H), 2.10 (s,3H,AcOH), 2.82–2.94 (dd,2H), 3.15–3.28 (m,2H), 3.34–3.56 (m,2H), 3.90–4.02 (m,4H), 4.26–4.35 (m,1H), 4.35–4.46 (m,1H)

Example 27
Synthesis of Compound 21 (acetate)

The title compound was synthesized in the same manner as Example 25 by using Asp(OBzl)-Ser(Bzl)-OBzl hydrochloride and Arg(Mts)-Arg(Mts)-OBzl hydrochloride.

Chloroform/methanol=95/5 was used as the eluent for the silica gel chromatography purification of the protected compound and 20% MeOH containing 0.1% acetic acid was used as the eluent for the liquid chromatography fractionation and purification of the final product.

FAB Mass $(M-CH_3COO)^+$ 619

$^1$H-NMR$_2$ (D$_2$O,$\delta$) 1.52–2.12 (m,8H), 2.10 (s,3H,AcOH), 2.80–3.00 (m,2H), 3.12–3.60 (m,6H), 3.90–3.94 (m,2H), 4.28–4.35 (m,2H), 4.35–4.44 (m,1H)

Example 28
Synthesis of Compound 22 (hydrochloride)

Maleic anhydride (0.98 g) and Asp(OBzl)-Ser(Bzl)-OBzl hydrochloride (5.26 g) were dissolved in tetrahydrofuran (20 ml) added with N-methylmorpholine (1.01 g) and stirred for 1 hour.

Subsequently, the reaction mixture was added with dicyclohexylcarbodiimide (2.06 g), Arg(Mts)OBzl hydrochloride (4.82 g) and N-methylmorpholine (2.02 g) and stirred overnight. The reaction mixture was concentrated under reduced pressure and the residue was dissolved in ethyl acetate and the organic layer was dried over anhydrous sodium sulfate. The ethyl acetate was evaporated under reduced pressure and the residue was subjected to silica gel chromatography to collect fractions of chloroform/methanol=95/5, of which solvent was evaporated under reduced pressure to give a protected compound (6.34 g).

The protected compound (1.00 g) was dissolved in a solution of 1M-trifluoromethanesulfonic acid, thioanisole and m-cresol in trifluoroacetic acid (20 ml) under ice cooling and stirred for 1 hour. Then, the reaction mixture was poured into ether and decantation was carried out. The residue was dissolved in deionized water and subjected to ion exchange treatment using Amberlite IRA-400 (hydrochloride) and treatment with activated carbon and lyophilized to give 370 mg of Compound 22 (hydrochloride).

FAB Mass $(M-Cl)^+$ 475

$^1$H-NMR (D$_2$O,$\delta$) 1.54–2.08 (m,4H), 2.10 (s,3H,AcOH), 2.82–2.94 (dd,2H), 3.15–3.28 (dd,2H), 3.90–3.94 (dd,2H), 4.28–4.36 (dd,1H), 4.36–4.44 (dd,1H), 6.30–6.38 (d,1H), 6.38–6.46 (d,1H)

Example 29
Synthesis of Compound 23 (hydrochloride)

The title compound was synthesized in the same manner as Example 28 by using Arg(Mts)-Gly-OBzl hydrochloride.

FAB Mass $(M-Cl)^+$ 532

Example 30
Synthesis of Compound 24 (hydrochloride)

The title compound was synthesized in the same manner as Example 28 by using succinic anhydride.

FAB Mass $(M-Cl)^+$ 477

$^1$H-NMR (D$_2$O,$\delta$) 1.54–2.08 (m,4H), 2.10 (s,3H,AcOH), 2.62 (brs,4H), 2.82–2.94 (dd,2H), 3.15–3.28 (dd,2H), 3.90–3.94 (dd,2H), 4.28–4.36 (dd,1H), 4.36–4.44 (dd,1H)

Example 31
Synthesis of Compound 25 (hydrochloride)

The title compound was synthesized in the same manner as Example 28 by using succinic anhydride and Arg(Mts)-Gly-OBzl hydrochloride.

FAB Mass $(M-Cl)^+$ 447

Example 32
Synthesis of Compound 26 (acetate)

The title compound was synthesized in the same manner as Example 1 by using Lys(Z)-OBzl hydrochloride.

FAB Mass $(M-CH_3COO)^+$ 348

Example 33
Synthesis of Compound 27 (acetate)

The title compound was synthesized in the same manner as Example 1 by using p-toluenesulfonic acid salt of Glu (OBzl)$_2$.

FAB Mass $(M-CH_3COO)^+$ 390

Example 34
Synthesis of Compound 28

Synthesis of ethylenediamine monomethacrylic acid amide

Ethylenediamine (6.0 g) was dissolved in tetrahydrofuran (100 ml) and added with methacrylic acid hydroxysuccinimide ester (16.9 g). Subsequently, the mixture was added with Boc anhydride (21.8 g) and added dropwise with a solution of diisopropylethylamine (12.9 g) in dimethylformamide (100 ml). After stirring overnight, the solvent was evaporated under reduced pressure and the residue was dissolved in ethyl acetate. The organic layer was washed with 10% aqueous solution of citric acid and dried over anhydrous sodium sulfate. The solvent was evaporated under reduced pressure and the residue was subjected to silica gel chromatography to collect fractions of dichloromethane/ethyl acetate=1/1 and the eluent was evaporated under reduced pressure.

Then, the residue was dissolved in dioxane (50 ml) and the Boc group was removed by adding a solution of 4M-hydrochloric acid in dioxane (50 ml) to give ethylenediamine monomethacrylic acid amide hydrochloride (4.0 g) Synthesis of beta-benzyloxy-L-aspartylaminoethylaminocarboxy-2-methylethene Boc-Asp(OBzl) (12.9 g) was dissolved in tetrahydrofuran (100 ml) and added with N-methylmorpholine (4.0 g) and isobutyl chloroformate (5.44 g) with cooling at -10° C. After stirring for 15 minutes, the mixture was added with ethylenediamine monomethacrylic acid hydrochloride (4.0 g) and N-methylmorpholine (3.0 g) and stirred. One hour later, the solvent was evaporated under reduced pressure and the residue was dissolved in chloroform. The organic layer was washed with saturated aqueous solution of sodium hydrogen carbonate and 10% aqueous solution of citric acid and dried over sodium sulfate. The solvent was evaporated under reduced pressure and the residue was subjected to silica gel chromatography to collect fractions of dichloromethane/ethyl acetate=25/75 to give N-Boc-β-benzyloxy-L-aspartylaminoethylaminocarbonyl-2-methylethene (3.3 g). N-Boc-β-benzyloxy-L-aspartylaminoethylaminocarbonyl-2-methylethene (3.3 g) was dissolved in dioxane (50 ml) and the Boc group was removed by adding 4M-hydrochloric acid solution in dioxane (50 ml) to give β-benzyloxy-L-aspartylaminoethylaminocarbonyl-2-methylethene (2.9 g).

Synthesis of L-arginyl-malonyl-L-aspartylaminoethylaminocarbonyl-2-methylethene

Malonic acid (2.05 g) and diphenylphosphorylazide (5.5 g) was dissolved in tetrahydrofuran (50 ml) and stirred. The mixture was added dropwise with Arg(Mts)-OBzl hydrochloride (4.83 g) and a suspension of N-methylmorpholine (3.03 g) in tetrahydrofuran (100 ml). The reaction mixture was added with N-methylmorpholine (2.02 g) so that the mixture have a pH of 7, stirred for 6 hours, added with diphenylphosphorylazide (2.75 g) and diisopropylethylamine (1.29 g) and allowed to react overnight. The reaction mixture was concentrated under reduced pressure and the residue was dissolved in ethyl acetate. The organic layer was washed with a saturated aqueous solution of sodium hydrogen carbonate and 10% aqueous solution of citric acid and dried over sodium sulfate to give HOOC—CH₂—CO-Arg (Mts)-OBzl (4.4 g).

HOOC—CH₂—CO-Arg(Mts)-OBzl (4.4 g), β-benzyloxy-L-aspartylaminoethylaminocarbonyl-2-methylketene (2.3 g) and diphenylphosphorylazide (3.6 g) were dissolved in dimethylformamide (100 ml) and added dropwise with N-methylmorpholine (2.4 g) at room temperature. After stirring overnight, the reaction mixture was concentrated under reduced pressure and the residue was dissolved in ethyl acetate. The organic layer was washed with 10% aqueous solution of citric acid and a saturated aqueous solution of sodium hydrogen carbonate and dried over sodium sulfate and the solvent was evaporated. The residue was subjected to silica gel chromatography to collect fractions of dichloromethane/methanol=95/5 to give a protected compound (0.84 g).

The protected compound (0.84 g) was dissolved in a solution of 1M-trifluoromethanesulfonic acid, thioanisole and m-cresol in trifluoroacetic acid (25 ml) with ice cooling and stirred for 1 hour. Then, the reaction mixture was poured into ether and decantation was carried out. The residue was dissolved in deionized water, subjected to ion-exchange treatment using Amberlite IRA-400 (hydrochloride) and lyophilized to give L-arginyl-malonyl-L-aspartylaminoethylaminocarbonyl-2-methylethene (0.43 mg).

Synthesis of Compound 28

L-arginyl-malonyl-L-aspartylaminoethylaminocarbonyl-2-methylethene (0.43 mg) was dissolved in nitrogen-substituted pure water (10 ml) and added with 10% aqueous solution of ammonium persulfate (0.5 ml) and 10% aqueous solution of sodium bisulfite (0.5 ml). Then, polymerization was carried out for 3 hours. Furthermore, the mixture was added with 10% aqueous solution of ammonium persulfate (0.5 ml) and 10% aqueous solution of sodium bisulfite (0.5 ml) and allowed to react for 3 hours. The reaction mixture was dialyzed against pure water using Spectrapore 6 (cut off: molecular weight of less than 3500) and lyophilized to give Compound 28 (250 mg).

Amino acid analysis (in 68 μg of the polymer) Arg 27.5 nmol, Asp 22.3 nmol

Example 35

Synthesis of Compound 29

Synthesis of β-benzyloxy-L-aspartic acid allyl ester hydrochloride

Boc-Asp(OBzl) (0.97 g), triethylamine (0.31 g) and allyl bromide (0.36 g) were dissolved in ethyl acetate (50 ml) and stirred for 3 hours under reflux condition. Then, the mixture was further added with allyl bromide (0.72 g) and stirred under reflux condition for 3 hours and then at room temperature overnight. The reaction mixture was evaporated under reduced pressure and the residue was dissolved in ethyl acetate. The organic layer was washed with 0.1M aqueous solution of citric acid and a saturated aqueous solution of sodium hydrogen carbonate and dried over sodium sulfate.

The ethyl acetate was evaporated under reduced pressure and the residue was subjected to silica gel chromatography to collect fractions of hexane/ethyl acetate=7/3 to give is N-Boc-β-benzyloxy-L-aspartic acid allyl ester (0.72 g). N-Boc-β-benzyloxy-L-aspartic acid allyl ester (0.72 g) was dissolved in dioxane (15 ml) and the Boc group was removed by adding 15 ml of 4M-hydrochloric acid solution in dioxane to give β-benzyloxy-L-aspartic acid allyl ester hydrochloride (0.40 g).

Synthesis of α-benzyloxy-Nω-trimethylbenzenesulfonyl-L-arginyl-malonyl-β-benzyloxy-L-aspartic acid Malonic acid (0.14 g), β-benzyloxy-L-aspartic acid allyl ester (0.40 g) and N-methylmorpholine (0.40 g) were dissolved in tetrahydrofuran (10 ml) and added dropwise with a solution of diphenylphosphorylazide (0.37 g) in tetrahydrofuran (10 ml) with stirring.

After stirring for 5 hours at room temperature, the mixture was added with diphenylphosphorylazide (0.37 g), Arg(Mts)-OBzl hydrochloride (0.65 g) and N-methylmorpholine (0.14 g) and stirred overnight. The reaction mixture was evaporated under reduced pressure and the residue was dissolved in ethyl acetate and washed with 0.1M aqueous solution of citric acid and a saturated aqueous solution of sodium hydrogen carbonate. The organic layer was dried over sodium sulfate. The ethyl acetate was evaporated under reduced pressure and the residue was subjected to silica gel chromatography to collect fractions of dichloromethane/methanol=97.5/2.5 to give α-benzyloxy-Nω-trimethylbenzenesulfonyl-L-arginyl-malonyl-β-benzyloxy-L-aspartic acid allyl ester (0.18 g).

Subsequently, the obtained allyl ester (0.083 g) was dissolved in tetrahydrofuran (1 ml), added with tetrakis (phenylphosphine)palladium (0.011 mg) and stirred, added with morpholine (0.086 g) and allowed to react overnight. The reaction mixture was evaporated under reduced pressure and the residue was dissolved in ethyl acetate. The organic layer was washed with 0.1M aqueous solution of citric acid and subsequently with a saturated aqueous solution of sodium hydrogen carbonate and dried over sodium sulfate. The ethyl acetate was evaporated to give α-benzyloxy-Nω-trimethylbenzenesulfonyl-L-arginyl-malonyl-β-benzyloxy-L-aspartic acid (0.020 g).

Synthesis of Nω-(α-benzyloxy-Nω-trimethylbenzenesulfonyl-L-arginyl-malonyl-β-benzyloxy-L-aspartyl)-L-lysine benzyl ester α-benzyloxy-Nω-trimethylbenzenesulfonyl-L-arginyl-malonyl-β-benzyloxy-L-aspartic acid (1.38 g) was dissolved in tetrahydrofuran (50 ml), added with carbonyldiimidazole (0.32 g) and then with Nα-Boc-L-lysine benzyl ester (0.60 g) and stirred overnight. The reaction mixture was evaporated under reduced pressure and the residue was dissolved in ethyl acetate. The organic layer was washed with 0.1M aqueous solution of citric acid and subsequently with a saturated aqueous solution of sodium hydrogen carbonate and dried over sodium sulfate.

The ethyl acetate was evaporated and the residue was subjected to silica gel chromatography to collect fractions of dichloromethane/methanol=95/5 to give Nα-Boc-Nω-(α-benzyloxy-Nω-trimethylbenzenesulfonyl-L-arginyl-malonyl-β-benzyloxy-L-aspartyl)-L-lysine benzyl ester (0.98 g). The protected compound (0.98 g) was dissolved in dioxane (20 ml) and the Boc group was removed by adding 25 ml of 4M-hydrochloric acid solution in dioxane to give Nω-(α-benzyloxy-Nω-trimethylbenzenesulfonyl-L-arginyl-malonyl-β-benzyloxy-L-aspartyl)-L-lysine benzyl ester hydrochloride (0.86 g).

Synthesis of Compound 29 (trimesic acid derivative)

Trimesic acid chloride (0.13 mg), Nω-(α-benzyloxy-Nω-trimethylbenzenesulfonyl-L-arginyl-malonyl-β-benzyloxy-L-aspartyl)-L-lysine benzyl ester hydrochloride (1.49 g) and triethylamine (0.16 g) were dissolved in tetrahydrofuran and stirred overnight. The reaction mixture was evaporated under reduced pressure and the residue was dissolved in ethyl acetate. The organic layer was washed with 0.1M aqueous solution of citric acid and subsequently with a saturated aqueous solution of sodium hydrogen carbonate and dried over sodium sulfate. The ethyl acetate was evaporated and the residue was again dissolved in ethyl acetate and added with a suitable amount of hexane to give a precipitate (1.3 g). The obtained precipitate was dissolved in a solution of 1M-trifluoromethanesulfonic acid, thioanisole and m-cresol in trifluoroacetic acid (30 ml) under ice cooling and stirred for 1 hour. Then, the reaction mixture was poured into ether and decantation was carried out. The residue was dissolved in deionized water and the aqueous layer was washed with ether and chloroform, subjected to ion exchange treatment using Amberlite IRA-400 (hydrochloride) and lyophilized to give 0.32 g of Compound 29.

Amino acid analysis (in 13 µg of the polymer) Arg: 20.2 nmol, Asp: 23.3 nmol, Lys: 22.9 nmol Example 36

Synthesis of Compound 30

Carbonyldiimidazole (0.16 g), Lys(Boc)-OBzl (0.70 g) and trimethylamine (0.21 g) were mixed and stirred overnight. The reaction mixture was evaporated under reduced pressure and the residue was dissolved in ethyl acetate. The organic layer was washed with 0.1M aqueous solution of citric acid and subsequently with a saturated aqueous solution of sodium hydrogen carbonate and dried over sodium sulfate. The ethyl acetate was evaporated under reduced pressure and the residue was dissolved in dichloromethane (25 ml), added with trifluoromethane (25 ml) and stirred for 30 minutes. The solvent was evaporated under reduced pressure to give a urea derivative (0.55 g).

The obtained urea derivative (0.36 g), α-benzyloxy-O-benzyl-L-seryl-β-benzyloxy-L-aspartyl-malonyl-Nω-trimethylbenzenesulfonyl-L-arginine (0.91 g) and dicyclohexylcarbodiimide (0.16 g) were dissolved in tetrahydrofuran (50 ml). The reaction mixture was evaporated under reduced pressure and the residue was dissolved in ethyl acetate. The organic layer was washed with 0.1M aqueous solution of citric acid and subsequently with a saturated aqueous solution of sodium hydrogen carbonate and dried over sodium sulfate. The ethyl acetate was evaporated and the residue was again dissolved in ethyl acetate and added with a suitable amount of hexane to give a precipitate (0.61 g).

The obtained precipitate was dissolved in a solution of 1M-trifluoromethanesulfonic acid, thioanisole and m-cresol in trifluoroacetic acid (30 ml) under ice cooling and stirred for 1 hour. Then, the reaction mixture was poured into ether and decantation was carried out. The residue was dissolved in deionized water, subjected to ion exchange treatment using Amberlite IRA-400 (hydrochloride) and lyophilized to give 0.20 g of Compound 30.

FAB Mass $(M-CH_3COO)^+$ 1003

Example 37

Synthesis of Compound 31

Polyethylene glycol monomethyl ether having an average molecular weight of 5000 (10 g) was dissolved in toluene (100 ml), added with sodium carbonate (5 g) and cyanuric chloride (1.1 g), stirred at 80° C. for 120 hours and allowed to cool to room temperature. The reaction mixture was filtered and the filtrate was added with hexane to cause crystallization. Then, the crystals were recrystallized from a solvent system of toluene, acetone and hexane to give white powder (7 g).

The obtained white powder (2.5 g), ethylenediamine (0.58 g) and triethylamine (1.01 g) were dissolved in chloroform (50 ml) and stirred at room temperature for 24 hours. The reaction mixture was evaporated under reduced pressure and the residue was dissolved in pure water, dialyzed by using Spectrapore 6 (cut off: molecular weight of not more than 1000) and lyophilized to give white powder (2.1 g)

α-benzyloxy-O-benzyl-L-seryl-β-benzyloxy-L-aspartyl-malonyl-Nω-trimethylbenzenesulfonyl-L-arginine (1.00 g) and carbonylimidazole (0.16 g) were dissolved in dimethylformamide (50 ml) and stirred, added dropwise simultaneously with a solution of the above-obtained PEG derivative (2.1 g) in chloroform (100 ml) and a solution of triethylamine (101 mg) in chloroform (50 ml) and stirred for 2 days.

The reaction mixture was evaporated under reduced pressure and the residue was dissolved in pure water, dialyzed against pure water by using Spectrapore 6 (cut off: molecular weight of not more than 3500) and lyophilized to give white powder (1.6 g). The obtained white powder was dissolved in acetic acid (50 ml), added with 10% palladium carbon (1.0 g) and subjected to hydrogenolysis at room temperature. Insolubles were removed by filtration through a Celite layer and the filtrate was concentrated under reduced pressure.

The residue was purified by DEAE Sephadex A-25 (eluent: Phosphate buffer) and dialyzed against pure water by using Spectrapore 6 (cut off: molecular weight of not more than 1000) and the dialysate was lyophilized to give Compound 31 (0.9 g).

Amino acid analysis (in 550 µg of the polymer) Arg: 26.5 nmol, Asp: 30.8 nmol, Ser: 21.3 nmol Example 38

Synthesis of Compound 32

Carbonylimidazole (0.81 g, 0.005 mol) was dissolved in dichloromethane (50 ml) and stirred. The solution was added dropwise with a suspension of triethylamine (0.51 g, 0.005 mol) and p-toluenesulfonic acid salt of aspartic acid dibenzyl ester (2.5 g, 0.005 mol) in dichloromethane (30 ml) at 10° C. and added with a suspension of Nω-diZ-arginine benzyl ester (2.84 g, 0.005 mol) and triethylamine (0.51 g, 0.005 mol) in dichloromethane. After stirring overnight, the reaction mixture was washed with water and separated and the organic layer was dried over magnesium sulfate. The mixture was filtered and the solvent was evaporated under reduced pressure. The residue was purified by silica gel column chromatography (eluent: ethyl acetate/hexane=1/1) to give a protected compound (1.2 g).

The obtained protected compound was suspended in methanol/acetic acid/water (40:10:5, 20 ml), added with Pd/C (0.5 g) and subjected to hydrogenolysis for 6 hours at room temperature. The reaction mixture was filtered through a Celite layer and the solvent was evaporated under reduced pressure. The obtained crystals were added with water (100 ml) and the water was evaporated under reduced pressure. Similar water addition and evaporation were repeated twice. The obtained crystals were washed with poured water to give Compound 32 (0.33 g).

FAB-Mass $(M+H)^+$ 362

Example 39
Synthesis of Compound 33

Oxalyl chloride (0.65 g, 0.005 mol) was dissolved in dichloromethane (50 ml) and stirred. The solution was added dropwise with a suspension of triethylamine (3.12 g, 0.031 mol) and p-toluenesulfonic acid salt of aspartic acid dibenzyl ester (2.5 g, 0.005 mol) in dichloromethane (30 ml) at 10° C. After stirring for 1 hour, the mixture was added with Nω-diZ-arginine benzyl ester (2.84 g, 0.005 mol) and triethylamine (0.51 g, 0.005 mol). After stirring overnight, the reaction mixture was washed with water and separated. The organic layer was dried over magnesium sulfate and filtered and the solvent was evaporated under reduced pressure. The residue was purified by silica gel column chromatography (eluent: ethyl acetate) to give a protected compound (1.8 g).

The obtained protected compound was suspended in methanol/acetic acid/water (40:10:5, 20 ml), added with Pd/C (0.5 g) and subjected to hydrogenolysis for 6 hours at room temperature. The reaction mixture was filtered through a Celite layer and the solvent was evaporated under reduced pressure. The obtained crystals were added with water (100 ml) and the water was evaporated under reduced pressure. Similar water addition and evaporation were repeated twice. The obtained crystals were washed with poured water to give Compound 33 (0.30 g).

FAB-Mass $(M+H)^+$ 362

Example 40
Synthesis of Compound 34 p-Toluenesulfonic acid salt of aspartic acid dibenzyl ester (2.5 g, 0.005 mol), potassium carbonate (5.60 g, 0.04 mol), potassium iodide (0.34 g, 0.002 mol) and diacetylacetamide (300 ml) were charged in a three-neck flask and stirred at 0° C.

This solution was added dropwise with bromoacetyl chloride (0.8 g, 0.005 mol) over 30 minutes and stirred for 1 hour. Then, the solution was added with Nω-diZ-arginine benzyl ester (2.84 g, 0.005 mol) and stirred for 4 hours while the reaction temperature was raised to 45° C. The reaction mixture was added gradually with 10% aqueous solution of citric acid aqueous solution and with ethyl acetate to extract it. The organic layer was separated, washed with a saturated aqueous solution of sodium hydrogen carbonate and then with water and dried over magnesium sulfate. The solvent was evaporated under reduced pressure and the residue was purified by silica gel column chromatography (eluent: dichloromethane/methanol=97/3) to give a protected compound (3.5 g). The protected compound (1.0 g) was suspended in methanol/acetic acid/water (40:10:5, 30 ml), added with Pd/C (2 g) and hydrogenated (6 hours, room temperature). The reaction mixture was filtered through a Celite layer and the solvent was evaporated under reduced pressure to give 0.27 g of Compound 34.

FAB-Mass $(M+H)^+$ 348

Example 41
Synthesis of Compound 35

Nω-diZ-arginine benzyl ester (2.84 g, 0.005 mol), potassium carbonate (5.60 g, 0.04 mol), potassium iodide (0.34 g, 0.002 mol) and dimetylacetamide (300 ml) were charged in a three-neck flask and stirred at 0° C. This solution was added dropwise with bromoacetyl chloride (0.8 g, 0.005 mol) over 30 minutes and stirred for 1 hour. Then, the solution was added with p-toluenesulfonic acid salt of aspartic acid dibenzyl ester (2.5 g, 0.005 mol) and stirred for 4 hours while the reaction temperature was raised to 45° C. The reaction mixture was added gradually with 10% aqueous solution of citric acid and with ethyl acetate to extract it. The organic layer was separated, washed with a saturated aqueous solution of sodium hydrogen carbonate and then with water and dried over magnesium sulfate. The solvent was evaporated under reduced pressure and the residue was purified by silica gel column chromatography (eluent: dichloromethane/methanol=97/3) to give a protected compound (3.8 g).

The protected compound was suspended in methanol/acetic acid/water (40:10:5, 30 ml), added with Pd/C (2 g) and hydrogenated (6 hours, room temperature). The reaction mixture was filtered through a Celite layer and the solvent was evaporated under reduced pressure to give 0.31 g of Compound 35.

FAB-Mass $(M+H)^+$ 348

Example 42
Synthesis of Compound 36 p-Toluenesulfonic acid salt of aspartic acid dibenzyl ester (300 g, 0.618 mol) was dissolved in tetrahydrofuran (750 ml) and added with acrylic acid (180 g, 2.50 mol) and triethylamine (313 g, 3.09 mol). After stirring for 2 hours at 60° C., the mixture was added with 18% hydrochloric acid and ethyl acetate to extract it. The organic layer was washed with water and then with a saturated aqueous solution of sodium hydrogen carbonate and left stand for 2 hours. The deposited crystals were taken by filtration. The obtained crystals were washed with poured ether to give a carboxylic acid (102 g).

The obtained carboxylic acid (1.92 g, 0.005 mol) and Nω-diZ-arginine benzyl ester (2.84 g, 0.005 mol) were dissolved in dichloromethane (30 ml) and added with triethylamine (0.51 g, 0.005 mol). The mixture was added with DCC (1.03 g, 0.005 mol) with ice cooling, stirred for 1 hour, turned to room temperature and stirred 3 hours. The reaction mixture was filtered and the solvent was evaporated under reduced pressure. The residue was dissolved in ethyl acetate, washed with 10% aqueous solution of citric acid and a saturated aqueous solution of sodium hydrogen carbonate and dried over magnesium sulfate. The solvent was evaporated under reduced pressure and the residue was purified by silica gel column chromatography (eluent: dichloromethane/methanol=97/3) to give a protected compound (3.42 g). The obtained protected compound was suspended in methanol/acetic acid/water (40:10:5, 30 ml), added with Pd/C (0.5 g) and subjected to hydrogenolysis for 6 hours at room temperature. The reaction mixture was filtered through a Celite layer and the solvent was evaporated under reduced pressure to give 0.33 g of Compound 36.

FAB-Mass $(M+H)^+$ 361

Example 43
Synthesis of Compound 36

Nω-diZ-arginine benzyl ester hydrochloride (4.35 g, 0.010 mol) was dissolved in tetrahydrofuran (50 ml) and added with acrylic acid (0.72 g, 0.010 mol) and triethylamine (0.11 g, 0.010 mol). After stirring for 2 hours at 60° C., the mixture was added with 18% hydrochloric acid and ethyl acetate to extract it. The organic layer was washed with water and then with a saturated aqueous solution of sodium hydrogen carbonate and left stand for 2 hours. The deposited crystals were taken by filtration. The obtained crystals were washed with poured ether to give a carboxylic acid (3.91 g).

The obtained carboxylic acid (3.02 g, 0.005 mol) and p-toluenesulfonic acid salt of aspartic acid dibenzyl ester (2.43 g, 0.005 mol) were dissolved in dichloromethane (30 ml) and added with triethylamine (0.51 g, 0.005 mol). The mixture was added with DCC (1.03 g, 0.005 mol) with ice cooling, stirred for 1 hour, brought back to room temperature and stirred for 3 hours. The reaction mixture was filtered and the solvent was evaporated under reduced pressure. The residue was dissolved in ethyl acetate, washed with 10% aqueous solution of citric acid and a saturated aqueous solution of sodium hydrogen carbonate and dried over magnesium sulfate. The solvent was evaporated under reduced pressure and the residue was purified by silica gel column chromatography (eluent: dichloromethane/methanol=97/3) to give a protected compound (3.61 g). The obtained protected compound was suspended in methanol/acetic acid/water (40:10:5), added with Pd/C (0.5 g) and subjected to hydrogenolysis for 6 hours at room temperature. The reaction mixture was filtered through a Celite layer and the solvent was evaporated under reduced pressure to give 0.29 g of Compound 36.

FAB-Mass (M+H)$^+$ 361

Example 44
Synthesis of Compound 38

Nα-Boc-Nε-Fmoc-L-Lys (14.5 g) was dissolved in DMF (dimethyl formamide) (150 ml) and added with NaHCO$_3$ (35.2 g) and benzyl bromide (24.4 g) dissolved in DMF (120 ml). After stirring for one day at room temperature, the mixture was added with water (200 ml) and extracted with ethyl acetate (250 ml). The organic layer was washed with water, dried over sodium sulfate, concentrated and purified by silica gel chromatography (n-hexane/ethyl acetate=50/50) to obtain a benzyl ester. The benzyl ester was dissolved in TFA (trifluoroacetic acid) (100 ml), stirred for one hour at room temperature and then evaporated to remove TFA. Ether was added to precipitate crystals which were then filtered and dried in vacuo to obtain TFA salt of Nε-Fmoc-L-Lys (OBn) (17.0 g).

BocArg(Mts) (13.7 g) was dissolved in DMF (150 ml), added with CDI (carbonyldiimidazole) (4.9 g) at 0° C. and stirred for one hour. The mixture was added with the TFA salt dissolved in DMF (50 ml) and diisopropylethylamine (3.9 g) and stirred for one hour at 0° C. and reacted overnight at room temperature. After removing the solvent in vacuo, the residue was dissolved in ethyl acetate and washed with 10% aqueous citric acid solution, saturated aqueous NaHCO$_3$ solution and saturated aqueous NaCl solution. The organic layer was dried over anhydrous sodium sulfate. Ethyl acetate was evaporated in vacuo. The residue was purified by silica gel chromatography (ethyl acetate) to obtain BocArg(Mts)-Nε-Fmoc-L-Lys(OBn) (20.1 g).

BocArg(Mts)-N-ε-Fmoc-L-Lys(OBn) was dissolved in TFA (100 ml), stirred for one hour at room temperature and then evaporated to remove TFA. Ether was added to precipitate crystals which were then filtered and dried in vacuo to obtain TFA salt of Arg(Mts)-Nε-Fmoc-L-Lys(OBn). N-carboxyethyl-L-aspartic acid dibenzyl ester (0.77 g) prepared in Example 42 and TFA salt of Arg(Mts)-Nε-Fmoc-L-Lys(OBn) (1.81 g) were dissolved in DMF/CH$_2$CH$_2$ (20 ml/20 ml), and added with HOBt (hydroxybenzotriazole) (0.31 g), DCC (dicyclohexylcarbodiimide) (0.41 g) and diisopropylethylamine (0.31 g). The mixture was reacted for one hour at 0° C. and for 16 hours at room temperature and filtered to remove the precipitate. After the solvent was evaporated in vacuo, the residue was dissolved in ethyl acetate (200 ml), and washed with 10% aqueous citric acid solution, saturated aqueous NaHCO$_3$ solution and saturated aqueous NaCl solution. The organic layer was dried over anhydrous sodium sulfate. The solvent was evaporated in vacuo. The residue was purified by silica gel chromatography (ethyl acetate/n-hexane=80/20) to obtain the protected compound (1.1 g).

The protected compound (1.1 g) was dissolved in THF (tetrahydrofuran) (15 ml), added with piperidine (3 ml) and reacted for one hour at room temperature. The reaction mixture was poured into n-hexane (40 ml). The precipitate was washed with n-hexane and then dissolved in methylene chloride. The solvent was evaporated in vacuo to obtain de-Fmoc derivative (0.77 g).

The de-Fmoc derivative (0.77 g) was dissolved in DMAc (dimethylacetamide) (10 ml), added under ice cooling with terephthaloyl chloride (0.088 g) in DMAc (3 ml) and diisopropylethylamine (0.10 g) and reacted for one hour at 0° C. and for additional 8 hours at room temperature. The reaction mixture was poured into water (300 ml). The precipitate was collected and washed with ether and purified by silica gel chromatography (methylene chloride/methanol=90/10) to obtain the protected derivative of Compound 38 (0.23 g).

The protected derivative of Compound 38 (0.23 g) was dissolved in a solution of 1M-trifluoromethane sulfonic acid, thioanisole and m-cresol in trifluoroacetic acid (10 ml) under ice cooling. The mixture was stirred for one hour and poured into ether to decant. The precipitate was dissolved in deionized water. The solution was subjected to ion-exchange treatment using Amberlite IRA-400 (hydrochloride), activated carbon treatment and then lyophilization to obtain Compound 38 (hydrochloride) (110 mg).

FAB-Mass (M+H)$^+$ 1109

Example 45
Synthesis of Compound 39

The same procedures as in Example 44 were repeated except that malonic acid mono (L-aspartic acid dibenzyl ester) amide (0.80 g) prepared in Example 4 was substituted for N-carboxyethyl-L-aspartic acid dibenzyl ester prepared in Example 44 to obtain Compound 39 (240 mg).

FAB-Mass (M+H)$^+$ 1137

Example 46
Synthesis of Compound 40

P-toluenesulfonate of (L-aspartic acid dibenzyl ester) (20.1 g) and succinic anhydride (4.8 g) were dissolved in methylene chloride (80 ml), added with diisopropylethylamine (5.17 g) under ice cooling and stirred for one hour and then reacted for 12 hours at room temperature. The reaction mixture was concentrated in vacuo. The residue was dissolved in ethyl acetate (250 ml). The solution was washed with 10% aqueous citric acid solution and water and dried over anhydrous sodium sulfate. The solvent was evaporated in vacuo to obtain colorless succinic acid (L-aspartic acid dibenzyl ester) amide (16.1 g).

The same procedures as in Example 44 were repeated except that succinic acid (L-aspartic acid dibenzyl ester)

amide (0.83 g) was substituted for N-carboxyethyl-L-aspartic acid dibenzyl ester prepared in Example 44 to obtain Compound 40 (190 mg).

FAB-Mass (M+H)$^+$ 1165

Example 47
Synthesis of Compound 41

P-toluenesulfonate of (L-aspartic acid dibenzyl ester) (4.85 g) and maleic anhydride (0.98 g) were dissolved in THF (20 ml), added with N-methyl morpholine (1.01 g), and stirred for one hour. The reaction mixture was concentrated in vacuo. The residue was dissolved in ethyl acetate (60 ml). The solution was washed with 10% aqueous citric acid solution and water and dried over anhydrous sodium sulfate. The solvent was evaporated in vacuo to obtain colorless maleic acid (L-aspartic acid dibenzyl ester) amide (3.70 g).

The same procedures as in Example 44 were repeated except that maleic acid mono (L-aspartic acid dibenzyl ester) amide (0.82 g) was substituted for N-carboxyethyl-L-aspartic acid dibenzyl ester to obtain Compound prepared in Example 44 to obtain Compound 41 (200 mg).

FAB-Mass (M+H)$^+$ 1161

Example 48
Synthesis of Compound 42

BocAsp(OBn) (9.70 g) was dissolved in DMF (50 ml) and added with CDI (5.19 g) under ice cooling. After reacting for one hour, the mixture was added with p-xylylenediamine (2.04 g) dissolved in DMF (50 ml) and stirred for one hour under ice cooling and reacted for four hours at room temperature. The reaction mixture was poured into water (1.5 l) and the precipitate was filtered. The precipitate was dissolved in ethyl acetate and washed with 10% aqueous citric acid solution, saturated aqueous NaHCO$_3$ solution and saturated aqueous NaCl solution. The organic layer was dried over anhydrous sodium sulfate, concentrated and dried in vacuo to obtain xylylenediamine-di(Boc-L-aspartic acid-β-benzyl ester)-amide (8.16 g). The compound was dissolved in TFA (60 ml), stirred for one hour at room temperature and then evaporated to remove TFA. Ether was added to precipitate crystals which were then filtered and dried in vacuo to obtain xylylenediamine-di(TFA salt of Boc-L-aspartic acid-β-benzyl ester)-amide (8.15 g).

BocArg(Mts) (6.39 g) was dissolved in DMF (100 ml), added with CDI (2.27 g) under ice cooling and reacted for one hour. The reaction mixture was added with xylylenediamine-di(TFA salt of Boc-L-aspartic acid-β-benzyl ester)-amide (5.42 g) and diisopropylethylamine (1.18 g) dissolved in DMF (20 ml) and reacted for one hour and for additional one hour at room temperature. The reaction mixture was poured into water (800 ml). The precipitate was filtered, dried and recrystalized from methylene chloride/methanol/ether to obtain xylylenediamine-di [Boc-Arg(Mts)Asp(OBn)]-amide (7.72 g).

The Boc protected compound (7.72 g) was dissolved in THF/methylene chloride (50 ml/10 ml) and reacted for one hour at room temperature. The solvent was evaporated in vacuo and ether was added to precipitate crystals. The crystals were filtered and dried in vacuo to obtain xylylenediamine-di[TFA salt of Arg(Mts)Asp(OBn)]-amide (7.7 g).

N-carboxyethyl-L-aspartic acid dibenzyl ester (2.31 g) prepared in Example 42 and xylylenediamine-di[TFA salt of Arg(Mts)Asp(OBn)]-amide (4.35 g) were dissolved in DMF (50 ml), added under ice cooling with HOBt monohydrate (0.92 g), WSC (??????). HCl (1.15 g) and stirred for two hours. The mixture was reacted for six hours at room temperature and poured into water (800 ml). The precipitate formed were collected and dissolved in methylene chloride/methanol. The solution was concentrated, and added with ether to obtain crystals. The crystals were purified by silica gel chromatography (methylene chloride) to obtain the protected compound (0.61 g).

The protected compound (0.61 g) was dissolved in a solution of 1M-trifluoromethane sulfonic acid, thioanisole and m-cresol in trifluoroacetic acid (15 ml) under ice cooling. The mixture was stirred for one hour and poured into ether to decant. The precipitate was dissolved in deionized water. The solution was subjected to ion-exchange treatment using Amberlite IRA-400 (hydrochloride), activated carbon treatment and then lyophilization to obtain Compound 42 (hydrochloride) (290 mg).

FAB-Mass (M+H)$^+$ 1053

Example 49
Synthesis of Compound 43

The same procedures as in Example 48 were repeated except that malonic acid mono(L-aspartic acid dibenzyl ester) amide (2.40 g) prepared in Example 4 was substituted for N-carboxyethyl-L-aspartic acid dibenzyl ester to obtain Compound 43 (hydrochloride) (310 mg).

FAB-Mass (M+H)$^+$ 1081

Example 50
Synthesis of Compound 44

The same procedures as in Example 48 were repeated except that succinic acid (L-aspartic acid dibenzyl ester) amide (2.48 g) prepared in Example 46 was substituted for N-carboxyethyl-L-aspartic acid dibenzyl ester to obtain Compound 44 (hydrochloride) (370 mg).

FAB-Mass (M+H)$^+$ 1109

Example 51
Synthesis of Compound 45

The same procedures as in Example 48 were repeated except that maleic acid (L-aspartic acid dibenzyl ester) amide (2.47 g) prepared in Example 47 was substituted for N-carboxyethyl-L-aspartic acid dibenzyl ester to obtain Compound 45 (hydrochloride) (340 mg).

FAB-Mass (M+H)$^+$ 1105

Example 52
Evaluation of stability under biochemical degradation condition

A test compound was dissolved in 20% solution of human plasma in PBS so that the solution containing the compound at a concentration of 1 mg/ml and incubated at 37° C. Remaining ratios of the compound at each of incubation periods were determined by high performance liquid chromatography (HPLC). The results are shown in FIG. 1.

HPLC conditions

Column: YMC ODS AQ (150×6 mm)

Detection: UV (A 210)

Eluent: 10 mM phosphate buffer (pH 2)/methanol [Compound 1 (95/5), RGDS (100/0)]

Flow rate: 1 ml/min

It is clear from the results that the amino acid derivative of the present invention is remarkably more stable under biochemical degradation condition and less likely to be degraded as compared with the cell adhesive peptide RGDS.

Example 53
Evaluation of platelet aggregation inhibition activity

Platelet aggregation inhibition activities of Compounds 1, 2, 3, 4, 5, 6, 7 and 15 were examined.

A test compound was added to PRP (polyplatelet rich plasma, $3 \times 10^8$ cells/ml) so that the plasma contained the compound at a concentration of 1 mg/ml and the plasma was added with 10 µl of ADP as an aggregation inducing substance. Five minutes later, aggregation ratio was determined by a chronologic whole blood aggregation ability measuring apparatus to calculate platelet aggregation inhibition ratio.

A segment peptide of fibronectin, Arg-Gly-Asp-Ser (RGDS), and Gly-Arg-Gly-Asp-Ser (GRGDS), of which tumour metastasis inhibition activities have been known, were used as comparative samples.

TABLE 1

| Test Compound | Platelet aggregation inhibition rate (%) | IC50 (µM) |
|---|---|---|
| RGDS | 100 | 180 |
| GRGDS | 100 | N.T. |
| Compound 1 | 57 | 2400 |
| Compound 2 | 53 | N.T. |
| Compound 3 | 50 | N.T. |
| Compound 4 | 48 | N.T. |
| Compound 5 | 48 | N.T. |
| Compound 6 | 49 | N.T. |
| Compound 7 | 44 | N.T. |
| Compound 15 | 47 | N.T. |

N.T.: not tested

It is clear from the above results that the compounds of the present invention have lower platelet aggregation inhibition activities as compared with the RGDS peptide.

It is also clear from the above results that the compounds of the present invention have weaker affinities for GPIIa/IIIb as compared with the compounds disclosed in WO 92/13552.

Example 54
Experimental metastasis test of B16-BL6 melanoma cells in lung

Tumor metastasis inhibition activities of the compounds of the present invention were examined.

A test compound and B16-BL6 melanoma cells, which have strong metastatic property, were mixed in PBS. 0.2 ml of the mixture was intravenously injected to each of C57BL/6 female mice, of which groups each consisted of 5 mice. The mixture injected (0.2 ml) contained $5 \times 10^4$ B16-BL6 cells. On the 14th day from the administration, number of melanoma cell colonies was determined and compared with that of control mice, which were administered with PBS. Test compounds, administration doses and the results are shown in Tables 2 to 11.

A segment peptide of fibronectin, Arg-Gly-Asp-Ser (RGDS), or Gly-Arg-Gly-Asp-Ser (GRGDS), of which tumour metastasis inhibition activities have been known, were used as comparative samples.

TABLE 2

| Test Compound | Dose (µg/mouse) | Number of colonies (Mean ± SD) | |
|---|---|---|---|
| PBS | — | 141 ± 16 | (112–158) |
| RGDS | 3000 | 86 ± 15 | (71–111) ** |
| Compound 1 | 1000 | 46 ± 10 | (33–56) *** |

T-test;
*** P < 0.001,
** P < 0.01,
* P < 0.02

TABLE 3

| Test Compound | Dose (µg/mouse) | Number of colonies (Mean ± SD) | |
|---|---|---|---|
| PBS | — | 81 ± 23 | (53–117) |
| RGDS | 1000 | 89 ± 23 | (55–122) |
| Compound 2 | 1000 | 3 ± 2 | (0–6) *** |
|  | 500 | 39 ± 13 | (21–59) *** |
| Compound 3 | 1000 | 3 ± 2 | (0–6) *** |
|  | 500 | 24 ± 18 | (13–60) *** |
| Compound 6 | 1000 | 37 ± 15 | (22–65) ** |
|  | 500 | 35 ± 15 | (18–49) ** |

T-test;
*** P < 0.001,
** P < 0.01,
* P < 0.02

TABLE 4

| Test Compound | Dose (µg/mouse) | Number of colonies (Mean ± SD) | |
|---|---|---|---|
| PBS | — | 96 ± 14 | (74–112) |
| RGDS | 1000 | 83 ± 14 | (63–105) |
| Compound 1 | 500 | 13 ± 6 | (7–25) *** |
| Compound 2 | 500 | 23 ± 9 | (12–34) *** |
| Compound 3 | 500 | 30 ± 14 | (18–50) ** |
| Compound 4 | 500 | 41 ± 23 | (18–76) *** |
| Compound 5 | 500 | 33 ± 12 | (19–47) *** |
| Compound 6 | 500 | 18 ± 3 | (14–22) *** |
| Compound 7 | 500 | 32 ± 10 | (31–67) *** |
| Compound 8 | 500 | 55 ± 12 | (35–95) *** |
| Compound 12 | 500 | 58 ± 20 | (61–131) ** |
| Compound 14 | 500 | 94 ± 26 | (52–105) |

T-test;
*** P < 0.001,
** P < 0.01,
* P < 0.02

TABLE 5

| Test Compound | Dose (µg/mouse) | Number of colonies (Mean ± SD) | |
|---|---|---|---|
| PBS | — | 118 ± 15 | (90–135) |
| RGDS | 1000 | 80 ± 23 | (52–109) * |
| Compound 1 | 1000 | 25 ± 8 | (17–40) *** |
| Compound 8 | 1000 | 24 ± 9 | (9–35) *** |
| Compound 12 | 1000 | 19 ± 6 | (10–27) *** |
| Compound 14 | 1000 | 69 ± 7 | (58–76) *** |

T-test;
*** P < 0.001,
** P < 0.01,
* P < 0.02

TABLE 6

| Test Compound | Dose (µg/mouse) | Number of colonies (Mean ± SD) | |
|---|---|---|---|
| PBS | — | 103 ± 30 | (66–163) |
| RGDS | 1000 | 132 ± 26 | (99–158) |
| Compound 1 | 500 | 63 ± 23 | (20–88) * |
| Compound 2 | 500 | 72 ± 15 | (60–87) |
| Compound 3 | 500 | 64 ± 22 | (29–90) * |
| Compound 4 | 500 | 76 ± 29 | (48–119) |
| Compound 5 | 500 | 70 ± 17 | (38–88) |
| Compound 6 | 500 | 85 ± 23 | (61–127) |
| Compound 7 | 500 | 89 ± 20 | (62–122) |
| Compound 15 | 500 | 39 ± 17 | (15–53) ** |
| Compound 17 | 500 | 154 ± 50 | (59–197) |
| Compound 18 | 500 | 70 ± 16 | (39–86) |

TABLE 6-continued

| Test Compound | Dose (μg/mouse) | Number of colonies (Mean ± SD) |
|---|---|---|

T-test;
*** $P < 0.001$,
** $P < 0.01$,
* $P < 0.02$

TABLE 7

| Test Compound | Dose (μg/mouse) | Number of colonies (Mean ± SD) | |
|---|---|---|---|
| PBS | — | 101 ± 28 | (61–133) |
| GRGDS | 500 | 93 ± 45 | (44–154) |
| Compound 1 | 500 | 19 ± 11 | (4–36) *** |
| Compound 2 | 500 | 38 ± 16 | (19–63) ** |
| Compound 15 | 500 | 32 ± 8 | (19–39) ** |
| Compound 16 | 500 | 97 ± 29 | (44–129) |

T-test;
*** $P < 0.001$,
** $P < 0.01$,
* $P < 0.02$

TABLE 8

| Test Compound | Dose (μg/mouse) | Number of colonies (Mean ± SD) | |
|---|---|---|---|
| PBS | — | 168 ± 28 | (121–195) |
| GRGDS | 1000 | 108 ± 17 | (85–121) *** |
| Compound 19 | 1000 | 32 ± 8 | (20–42) *** |
| Compound 20 | 1000 | 28 ± 9 | (18–43) *** |
| Compound 21 | 1000 | 25 ± 9 | (10–33) *** |
| Compound 22 | 1000 | 18 ± 11 | (8–35) *** |
| Compound 24 | 1000 | 55 ± 8 | (45–67) *** |

T-test;
*** $P < 0.001$,
** $P < 0.01$,
* $P < 0.02$

TABLE 9

| Test Compound | Dose (μg/mouse) | Number of colonies (Mean ± SD) | |
|---|---|---|---|
| PBS | — | 168 ± 28 | (121–195) |
| GRGDS | 1000 | 108 ± 17 | (85–121) ** |
| Compound 19 | 1000 | 32 ± 8 | (20–42) ** |
| Compound 20 | 1000 | 28 ± 9 | (18–43) *** |
| Compound 21 | 1000 | 25 ± 9 | (10–33) *** |

T-test;
*** $P < 0.001$,
** $P < 0.01$,
* $P < 0.02$

TABLE 10

| Test Compound | Dose (μg/mouse) | Number of colonies (Mean ± SD) | |
|---|---|---|---|
| PBS | — | 237 ± 29 | (176–259) |
| RGDS | 1000 | 234 ± 22 | (204–254) |
| Compound 28 | 1000 | 134 ± 18 | (112–164) *** |
| Compound 29 | 1000 | 135 ± 19 | (107–160) *** |
| Compound 30 | 1000 | 119 ± 15 | (108–145) *** |

T-test;
*** $P < 0.001$,
** $P < 0.01$,
* $P < 0.02$

TABLE 11

| Test Compound | Dose (μg/mouse) | Number of colonies (Mean ± SD) | |
|---|---|---|---|
| PBS | — | 114 ± 28 | (81–169) |
| RGDS | 1000 | 114 ± 24 | (73–126) |
| Compound 33 | 500 | 51 ± 18 | (31–84) *** |
| Compound 34 | 500 | 51 ± 19 | (31–84) *** |
| Compound 35 | 500 | 52 ± 14 | (37–75) *** |
| Compound 36 | 500 | 60 ± 14 | (48–79) ** |
| Compound 37 | 500 | 50 ± 12 | (31–74) *** |

T-test;
*** $P < 0.001$,
** $P < 0.01$,
* $P < 0.02$

As seen from the above results, the compounds of the present invention showed high activity for inhibiting metastasis of B16-BL6 melanoma cells to lung.

It was shown from the results of Tables 2 and 3 that the activity of the compounds are maintained irrespective of the steric configuration, R or S, of the compounds.

It was shown from the results of Tables 3, 4 and 6 that preferred $A^2$ is —$CH_2$—, —$CH_2$=$CH_2$—, —$CH_2$—$CH_2$— and —$C_6H_4$—.

It was shown from the results of Tables 4 and 5 that, when $L^1$ or $L^2$ is absent, it is preferred that at least one of $R^1$—X— and $R^2$—Y— is a hydroxyl group and particularly preferred that both of them are hydroxyl groups.

It was shown from the results of Tables 6, 7, 8 and 9 that preferred $L^1$ is glycine or arginine residue, and preferred $L^2$ is serine or glutamic acid residue.

Example 55

A test compound and L5178Y-ML25 T-lymphoma cells were mixed in PBS. 0.2 ml of the mixture was intravenously injected to each of CDF1 mice, of which groups each consisted of 5 mice. The mixture injected (0.2 ml) contained 4×10⁴ L5178Y-ML25 T-lymphoma cells. On the 14th day from the administration, weights of livers and spleens of mice were determined and compared with those of control mice, which were administered with PBS. Test compounds, administration doses and the results are shown in Table 12.

A segment peptide of fibronectin, Arg-Gly-Asp-Ser (RGDS), of which tumour metastasis inhibition activities have been known, was used as a comparative sample.

TABLE 12

| Test Compound | Dose (μg/mouse) | Weight of liver (Mean ± SD) | Weight of spleen (Mean ± SD) |
|---|---|---|---|
| PBS | — | 4.18 ± 0.30 | 0.23 ± 0.03 |
| Compound 1 | 1000 | 1.84 ± 0.36*** | 0.14 ± 0.01*** |
| Compound 1 | 500 | 2.98 ± 0.29*** | 0.20 ± 0.02 |
| Compound 1 | 100 | 3.09 ± 0.78** | 0.18 ± 0.02 ** |
| RGDS | 1000 | 3.83 ± 0.15 | 0.20 ± 0.03 |
| No lymphoma cell | — | 1.36 ± 0.02 | 0.12 ± 0.02 |

T-test;
*** $P < 0.001$,
** $P < 0.01$

Example 56

Experimental metastasis test of colon 26/M3.1 cells in lung

A test compound and colon 26/M3.1 cells, which have strong metastatic property, were mixed in PBS. 0.2 ml of the mixture was intravenously injected to each of C57BL/6 female mice, of which groups each consisted of 5 mice. The mixture injected (0.2 ml) contained 4×10⁴ colon 26/M3.1 cells. On the 14th day from the administration, number of colonies in lung was determined and compared with that of control mice, which were administered with PBS. Test compounds, administration doses and the results are shown in Table 13.

A segment peptide of fibronectin, Gly-Arg-Gly-Asp-Ser (GRGDS), of which tumour metastasis inhibition activities have been known, was used as a comparative sample.

TABLE 13

| Test Compound | Dose (μg/mouse) | Number of colonies (Mean ± SD) | |
|---|---|---|---|
| PBS | — | 148 ± 12 | (137–170) |
| GRGDS | 1000 | 111 ± 19 | (90–134) ** |
| Compound 1 | 1000 | 31 ± 26 | (4–63) *** |

T-test;
*** P < 0.001,
** P < 0.01,
* P < 0.02

It is clear from the results of Examples 55 and 56 that compounds of present invention are also effective for various tumors.

The amino acid derivatives of the present invention and pharmaceutically acceptable salts thereof can be administered to patients as an agent for inhibiting tumor metastasis, which contains at least one of the compounds and, optionally, a conventional carrier as well as pharmaceutical auxiliaries. Their daily dose may be in a range of from 0.2 μg/kg to 600 mg/kg (body weight of patient) and determined depending on symptoms, ages, body weights of patients and the like.

The compounds of the present invention and salts are preferably administered by methods generally used for peptide drugs, for example, by parenteral administration methods such as intravenous administration, intramuscular administration and subcutaneous administration. In order to prepare injections, for example, the compounds of the present invention or salts thereof may be dissolved in PBS or physiological saline. Further, lyophilized drugs may be prepares by dissolving them in about 1N acetic acid and lyophilizing the solution. Those formulations may contain a conventional stabilizer such as glycine and albumin.

Moreover, if the drugs are prepared in the form of microcapsules composed of liposomes containing the compounds, microspheres or hydrogel, they may be administered orally and, if they may be prepared in the form of sappositories, sublingual tablets, nasal sprays or the like, they may be absorbed from mucosae other than those of digestive tract.

The compound of the present invention are remarkably more stable and less likely to be degraded under biochemical degradation conditions as compared with conventional cell adhesive peptides and, moreover, show very strong activity for inhibiting tumor matastasis. Further, they show weaker platelet aggregation inhibition activity as compared with known RGDS and GRGDS peptides, namely, they show the activity to an extent corresponding to less than about one tenth of that of RGDS peptide. Therefore, they show selectivity with respect to the activity for inhibiting tumor metastasis and particularly useful as agents for inhibiting tumor metastasis.

To the inventors' knowledge, there have not been disclosed any compounds which show weak platelet aggregation activity or anticoagulation activity and remarkably high activity for inhibiting tumor metastasis like the amino acid derivatives of the present invention.

We claim:

1. An amino acid derivative represented by the following general formula (I):

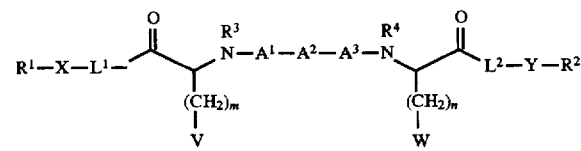

wherein;

$L^1$ and $L^2$ represent a residue which may be present or absent and, when they are present, they independently represent a natural or synthetic amino acid residue or a peptide residue;

$A^1$ and $A^3$ represent C=O and $A^2$ represents a linear or branched alkylene group having 1 to 3 carbon atoms or a cyclic alkylene group having 4 to 8 carbon atoms or a phenylene group, which may have one or more substituents and unsaturated groups;

$A^1$, $A^2$ and $A^3$ may be present or absent, provided that at least one of $A^1$, $A^2$ and $A^3$ must be present;

m represents an integer of 1 to 5, M represents an integer of 1 to 3, and they may be the same or different from each other;

V represents a guanidino group or an amino group;

W represents —COOH;

$R^1$ and $R^2$ independently represent a hydrogen atom, a linear or branched alkyl, aryl, arylalkyl group or a heterocyclic residue, which have 1 to 20 carbon atoms and which may have one or more substituents and unsaturated groups;

$R^3$ and $R^4$ independently represent a hydrogen atom or a methyl group;

X and Y independently represent —NH— or —O—; and steric configurations of asymmetric carbon atoms present in the compounds may be any of R, S and RS;

except for those compounds of the formula (I) wherein both of $L^1$ and $L^2$ are absent and both of $A^1$ and $A^3$ are C=O, $A^2$ is —CH$_2$—, X is —NH—, and $R^2$ is a phenyl group, a naphthyl group or a heterocyclic residue, which may have 1 to 3 substituents, and wherein both or one of $R^1$—X— and $R^2$—Y— represent a hydroxyl group;

or a pharmaceutically acceptable salt thereof.

2. A compound of claim 1 wherein m is 3 or 4 and n is 1 or 2.

3. A compound of claim 2 wherein n is 1 and V represents guanidino group.

4. A compound of claim 1 wherein —A¹—A²—A³— is selected from the group consisting of —CO—CH₂—CO—, —CO—(CH₂)₂—CO—, —CO—(CH₂)₃—CO—, —CO—CH=CH—CO—, —CO—C(CH₃)₂—CO—, —CO—C₆H₄—CO—, —CO—, —CO—CO—, —CO—CH₂—, —CH₂—CO—, —CH₂—CH₂—CO— and —CO—CH₂—CH₂—.

5. A compound of claim 4 wherein —$A^1$—$A^2$—$A^3$— represents —CO—$CH_2$—CO—.

6. A compound of claim 5 wherein $L^1$ is present and represents a residue selected from the group consisting of glycine and arginine residues.

7. A compound of claim 5 wherein $L^2$ is present and represents a residue selected from the group consisting of serine, aspartic acid and glutamic acid residues.

8. A compound of claim 4 wherein —$A^1$—$A^2$—$A^3$— represents —CO—$(CH_2)_2$—CO—, —CO—CH=CH—CO— or —CO—$C_6H_4$—CO—.

9. A compound of claim 8 wherein $L^1$ is present and represents a residue selected from the group consisting of glycine and arginine residues.

10. A compound of claim 8 wherein $L^2$ is present and represents a residue selected from the group consisting of serine, aspartic acid and glutamic acid residues.

11. A compound of claim 4 which is represented by any one of the following formulae;
$Arg_{rev}$-$COCH_2CO$-Asp,
$Arg_{rev}$-$COCH_2CO$-Asp-Ser,
$Arg_{rev}$-$COCH_2CO$-Asp-Asp,
$Gly_{rev}$-$Arg_{rev}$-$COCH_2CO$-Asp,
$Arg_{rev}$-$Arg_{rev}$-$COCH_2CO$-Asp,
$Gly_{rev}$-$Arg_{rev}$-$COCH_2CO$-Asp-Ser,
$Arg_{rev}$-$Arg_{rev}$-$COCH_2CO$-Asp-Ser,
$Arg_{rev}$-$COCH_2CH_2CO$-Asp,
$Arg_{rev}$-$COCH_2CH_2CO$-Asp-Ser,
$Gly_{rev}$-$Arg_{rev}$-$COCH_2CH_2CO$-Asp,
$Arg_{rev}$-$Arg_{rev}$-$COCH_2CH_2CO$-Asp,
$Gly_{rev}$-$Arg_{rev}$-$COCH_2CH_2CO$-Asp-Ser,
$Arg_{rev}$-$Arg_{rev}$-$COCH_2CH_2CO$-Asp-Ser,
$Arg_{rev}$-COCH=CHCO-Asp,
$Arg_{rev}$-COCH=CHCO-Asp-Ser,
$Gly_{rev}$-$Arg_{rev}$-COCH=CHCO-Asp,
$Arg_{rev}$-$Arg_{rev}$-COCH=CHCO-Asp,
$Gly_{rev}$-$Arg_{rev}$-COCH=CHCO-Asp-Ser
$Arg_{rev}$-$Arg_{rev}$-COCH=CHCO-Asp-Ser,
wherein "rev" indicates that the amino acid is connected inversely and a carboxyl terminus of terminal amino acid residue of the compound may be optionally alkylamidated, aralkylamidated or alkyl esterified.

12. A compound of claim 1 wherein —$A^1$—$A^2$—$A^3$— is selected from the group consisting of —CO—, —CO—CO—, —CO—$CH_2$—, —$CH_2$—CO—, —$CH_2$—$CH_2$—CO— and —CO—$CH_2$—$CH_2$—.

13. A compound of claim 12 which is represented by any one of the following formulae;
$Arg_{rev}$-CO-Asp,
$Arg_{rev}$-CO—CO-Asp,
$Arg_{rev}$-$COCH_2$-Asp,
$Arg_{rev}$-$CH_2CO$-Asp,
$Arg_{rev}$-$CH_2CH_2CO$-Asp, and
$Arg_{rev}$-$COCH_2CH_2$-Asp,
wherein "rev" indicates that the amino acid is connected inversely.

14. A compound composed of a macromolecular carrier to which at least one compound of claim 1 is bonded by a covalent bond.

15. A compound of claim 14 wherein the macromolecular carrier is selected from the group consisting of polysaccharides having amino groups or carboxyl groups, polyacrylic acid and polymethacrylic acid.

16. A compound composed of an organic molecule to which a plural number of the compounds of claim 1 are bonded by covalent bonds.

17. A compound of claim 16 wherein the organic molecule is selected from the group consisting of oligosaccharides and monosaccharides having 1 to 6 amino groups, carboxyl groups or sulphonate groups.

18. A compound of claim 16 wherein the organic molecule is selected from the group consisting of benzene derivatives and naphthalene derivatives having 1 to 3 amino groups or carboxyl groups.

19. A tumor metastasis inhibitor comprising an effective amount of a compound of claim 1 as an active ingredient and a pharmaceutically acceptable carrier or diluent.

20. A tumor metastasis inhibitor comprising an effective amount of a compound of claim 14 as an active ingredient and a pharmaceutically acceptable carrier or diluent.

21. A tumor metastasis inhibitor comprising an effective amount of a compound of claim 16 as an active ingredient and a pharmaceutically acceptable carrier or diluent.

* * * * *

UNITED STATES PATENT AND TRADEMARK OFFICE
CERTIFICATE OF CORRECTION

PATENT NO. : 5,763,408

DATED : June 9, 1998

INVENTOR(S) : Nishikawa, et al.

It is certified that error appears in the above-identified patent and that said Letters Patent is hereby corrected as shown below:

Column 48, line 33, change "M" to --n--.

Signed and Sealed this

Twenty-third Day of February, 1999

Attest:

Q. TODD DICKINSON

*Attesting Officer*      *Acting Commissioner of Patents and Trademarks*